(12) United States Patent
Wartenfeld et al.

(10) Patent No.: US 10,297,343 B1
(45) Date of Patent: May 21, 2019

(54) FACILITATING COMPUTERIZED INTERACTIONS WITH EMRS

(71) Applicant: DBMOTION LTD., Hod Hasharon (IL)

(72) Inventors: Robert Wartenfeld, Moshav Ge'alya (IL); Ziv Ofek, Meitar (IL); Eyal Greenberg, Meitar (IL); Ziv Gome, Beit Kama (IL); Shiri Ben-Tal, Omer (IL)

(73) Assignee: DBMOTION LTD., Hod Hasharon (IL)

( * ) Notice: Subject to any disclaimer, the term of this patent is extended or adjusted under 35 U.S.C. 154(b) by 1 day.

(21) Appl. No.: 14/145,904

(22) Filed: Dec. 31, 2013

Related U.S. Application Data

(63) Continuation of application No. 13/208,417, filed on Aug. 12, 2011, which is a continuation-in-part of application No. 12/840,806, filed on Jul. 21, 2010.

(Continued)

(51) Int. Cl.
*G06Q 10/10* (2012.01)
*G06Q 50/22* (2018.01)
*G16H 10/60* (2018.01)

(52) U.S. Cl.
CPC .......... *G16H 10/60* (2018.01); *G06Q 10/10* (2013.01); *G06Q 50/22* (2013.01)

(58) Field of Classification Search
CPC .............. G06Q 50/22; G06Q 50/24; G06F 19/322–19/327; G16H 10/00; G16H 10/20; G16H 10/40; G16H 10/60; G16H 10/65; G16H 15/00; G16H 20/00; G16H 20/10; G16H 20/13; G16H 20/17;

(Continued)

(56) References Cited

U.S. PATENT DOCUMENTS

2002/0032583 A1* 3/2002 Joao .................................. 705/2
2002/0083075 A1* 6/2002 Brummel .............. G06Q 50/22

(Continued)

OTHER PUBLICATIONS

Lahteennnaki et al, "Interoperability of Personal Health Records," Engineering in Medicine and Biology Society, 2009, Annual International Conference of the IEEE, 1726-1729 (Year: 2009).*

(Continued)

*Primary Examiner* — Minnah L Seoh
*Assistant Examiner* — William G Lultschik
(74) *Attorney, Agent, or Firm* — Medley, Behrens & Lewis, LLC

(57) ABSTRACT

A method for using a health information exchange system which stores patient record data regarding a multiplicity of patients, to serve a first plurality of EMRs each interacting with an EMR community including a set of at least one EMR, the method comprising: for each individual EMR within the first plurality of EMRs, performing a computerized context interception process using a processor to intercept context from the individual EMR and to identify there within an event whereby a health provider using the individual EMR calls up an individual patient's record from said individual EMR; and responsive to identification of the event, using a computerized output device for providing patient record data, pertaining to the individual patient, to the health provider.

20 Claims, 50 Drawing Sheets

Related U.S. Application Data

(60) Provisional application No. 61/438,762, filed on Feb. 2, 2011.

(58) Field of Classification Search
CPC ........ G16H 20/30; G16H 20/40; G16H 20/60; G16H 20/70; G16H 20/90; G16H 30/00
See application file for complete search history.

(56) References Cited

U.S. PATENT DOCUMENTS

| | | | |
|---|---|---|---|
| 2006/0074633 A1* | 4/2006 | Mahesh | G06F 19/321 704/9 |
| 2008/0046292 A1* | 2/2008 | Myers et al. | 705/3 |
| 2009/0177492 A1* | 7/2009 | Hasan et al. | 705/3 |

OTHER PUBLICATIONS

Hussain et al, "Healthcare Applications Interoperability through Implementation of HL7 Web Service Basic Profile," 2009 Sixth International Conference on Information Technology: New Generations, 308-313 (Year: 2009).*

* cited by examiner

| Example of Applicant Specific Requirements – Content/VPO Analyzer | Pr. |
|---|---|
| Retrieved data typically should comply with the standard HIES security policy (such as patient context, user context and role, privacy and security) | P0 |
| "Exclude mine" rule – Present Clinical data that is not available in the EHR in the user works with.<br>This rule can be implemented in several level:<br>1. By Source – Basic – All Acts which received from my EHR source.<br>2. By Source – Advanced – All Acts which coming from my EHR as well as sources of my EHR (e.g. Labs which flows to both Allscripts and HIES, typically should not be presented when the EHR is Allscripts) | P0 |
| In continue to previous<br>3. Semantically – in addition to #1 and #2, exclude acts which are semantically equivalent to information available in my EHR. | P2 |
| "new since last seen" rule – get all clinical acts (new or updated) since last time I accessed HIES Clinical Viewer. E.g. if user access Problems page in clinical viewer or in SmartAgent on 1/1/2010. Then when rule is applied, the results will include all problems new in HIES since 1/1/2010. | P1 |
| Extensibility – It typically should be possible to add new rules in extensible way. Preferably – without need for new product version. | P0 |
| The handled context typically should include:<br>User<br>Patient<br>Application Type (Allscripts EEHR, MyWay, Cerner, EPIC, Sunrise, etc.)<br>EHR Application Identifier (Allscripts EEHR in JUP, Cerner H1 and H2 in UPMC, etc.)<br>Workflow Context (Optional. E.g. which Tab the user selected in the EHR) | P0 |

FIG. 1b

| Example of Applicant Specific Requirements - Context Capturing and Sharing | Pr. |
|---|---|
| To facilitate integration with EHR which voluntarily shares context with HIES, there typically should be a simple, standard (preferred) way to enable the EHRs written in different technologies (such as Java, web, .Net, C++, etc.) to share the context (user, patient, application and workflow ). | P0 |
| In case EHR cannot share context, It typically should be possible to proactively capture the following context elements: , Application ID ,patient (MRN), User (Username, User Details), from the EHR screen (without any development from the EHR side) | P0 |
| It typically should be possible to capture workflow operations (e.g. access to Labs/Meds pages) | P2 |
| Ability to support different versions of an her | P2 |
| In case NO MRN is available, It typically should be possible to capture demographics for EMPI search | P2 |
| Extendibility - It typically should be possible to extend capturing support for different EHRs. Preferably as an extension points configured by eth professional service. | P1 |

FIG. 1c

| | |
|---|---|
| Semantic Search | |
| Enable semantic search over codified patient data. | P2 |
| e.g. Search for Beta Blockers or Hemoglobin HbA1c typically should find results for codes that are semantically related to those codes – either directly or through concepts connections. | |
| Enable semantic search over unstructured patient data (e.g. clinical documents, acts notes, descriptions, etc.). | P2 |
| Configurations | |
| It typically should be possible to configure which rules will presentation and their order. | P1 |
| It typically should be possible to personalize configurations. | P1 |
| Personalized configuration typically should be user driven and NOT machine driven. | P1 |
| Configurations typically should be kept on the centralized server side as much as possible, and prevent as much as possible local machine wise configurations. | P1 |

FIG. 1d

| Example of Applicant Specific Requirements - Floating Application | Pr. |
|---|---|
| Create a HIES Client Application (AKA SmartAgent) that presents information from HIES within the EMR context and workflow. | P0 |
| The HIES SmartAgent typically should NOT be dependent on development for integration by the EMR side. Instead it should have its own capability to support different EMRs written in different technologies. | |
| The floating application should be bound to a specific active instance of an EMR (as the user might work with several EMR applications in parallel). | P0 |
| The user experience should fit the EMR UI as much as possible (position, application binding, size, etc). | P0 |
| The solution's UI typically should NOT cause any interruptions to the user's regular workflow. Rather, provide clear indications. | P1 |
| To meet different EMR's look and fill and user preferences, there typically should be an ability to apply skins/configure appearance of elements such as UI color, icons/buttons and fonts | P0 |
| The SmartAgent typically should present the data in a summarized way taking into consideration the Application limited space. | P0 |
| Serve as a user-friendly gateway to other HIES applications, such as Clinical Viewer, Collaborate and other future HIES Application. | P0 |
| At any point, it typically should be easy for the user to return to the regular workflow – i.e. easy hiding/closing of the UI. | P0 |
| Ability to View Results/Clinical in printable format and print it. | P1 |
| Ability to View HIES Collaborate Recent Events and do actions such as File, Reminders, Referrals, Etc. | P1 |
| Ability to perform HIES collaborate Actions such as "File", "Print", "Referral" etc. | P1 |

FIG. 1e

| Example of Applicant Specific Requirements - | Pr. |
|---|---|
| 1.1.1 Auditing | |
| SmartAgent and VPO Analyzer – Relevant navigation operations and failures in the SmartAgent typically should be audited in the HIES Auditing System (STL). | P1 |
| SmartAgent – it typically should be possible to extract from STL what Clinical Aspects (Problems, Labs etc.) the user accessed. In the same way the clinical viewer auditing behaves. | P1 |
| 1.1.2 Security | |
| Authentication – there typically should be manual log-in option | P1 |
| Authentication – There typically should be a windows SSO authentication support | P2 |
| Authentication – The SmartAgent typically should be able to generate SAML token based on the user identity captures or provided by the EHR. | P1 |
| SmartAgent and VPO Analyzer – security authorization operations typically should be applied according to the standard HIES security policy. | P1 |
| 1.1.3 Localization | |
| There typically should be an internationalization support including presentation in different languages, ability to translate captions and text, capturing elements from screens in different languages. | P2 |
| There typically should be an ability to present right-to-left text and open panels to both right and left directions. | P2 |

FIG. 2a

| Topology and pre-requisites | |
|---|---|
| The solution typically should support deployment of the SmartAgent either on Local machine and on Citrix (or Citrix alike products) | P0 |
| SmartAgent typically should support windows XP and Windows 7 Operations Systems | P0 |
| It is expected to have the SmartAgent User interface be able to reused as part of solution for Non windows platforms such as iPhone, iPad, blackberry Android etc. | P3 |
| It is NOT expected to have the windows based solution be used as is (screen capturing, deployment, etc.) on non windows platforms | |
| It typically should be possible to easily apply ongoing updates for the SmartAgent without requiring the user initiating the process. Including presentation updates, capturing updates, more EHR supports. | P1 |
| It typically should be possible to deploy the SmartAgent as a download from a website (e.g. ClickOnce installation). | P1 |
| It typically should be possible to deploy the SmartAgent in distribution mode (in case of corporate control machines). | P1 |
| The SmartAgent installation typically should include ALL required components including 3$^{rd}$ party .NET frameworks etc. We typically should NOT assume any pre-requisites beside OS. | P1 |

FIG. 2b

| 1.1.4 Performance | |
|---|---|
| Expected response time from getting into patient record in the EHR until presenting data from HIES in HIES within the SmartAgent typically should be - 1 Second. Worst case – 2 Seconds. | P0 |
| User experience for any action within the SmartAgent typically should look seamless to the user (under 0.5 Seconds) | P0 |

FIG. 2c

| 1.1.5 Reusability and integrability | |
|---|---|
| The SmartAgent typically should use as much as possible existing pages from the clinical Viewer and CareBoard in embedded panels of the SmartAgent. | P0 |
| The Clinical Viewer and CareBoard must take into consideration in the design the ability to the other applications such as the SmartAgent to be able to use internal modules (e.g. use module of Laboratory page" or "My Recent Events" as a component within the SmartAgent Panel. | P1 |
| The SmartAgent typically should take into consideration the ability to reuse the modules in other HIES Applications such as Clinical Viewer and CareBoard. | P2 |

FIG. 2d

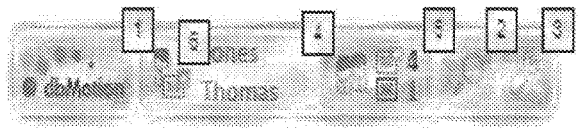

FIG. 3b

| Footnote | Label | Interactions | Description |
|---|---|---|---|
| 1 | HIESLaunchButton | OnClick:<br>  Launch HIES Clinical Viewer | This Button opens the HIES Clinical Viewer with the Patient and User context. |
| 2 | SearchButton | OnClick:<br>  Enable Search:<br>    Set Floating Application Small Panel state to FloatingSearchOpen | |
| 3 | ToolsButton | OnClick:<br>  Enable Configurations:<br>    Set Floating Application Small Panel state to FloatingToolOpen | |
| 4 | Patient Info | OnClick:<br>  OpenMainPanel: | |
| 5 | Collaborate Button | OnClick:<br>  Open Collaborate Recent Events: | |
| 6 | Recent Events Button | OnClick:<br>  Open Recent Events: | |

FIG. 3c

FIG. 3d

| Footnote | Label | Interactions |
|---|---|---|
| 4 | File All | OnClick:<br>  File CareEvent:<br>    Show GrayBackground - Below Agent, Preview Panel<br>    Set Preview Panel state to File - All Acts |
| 5 | CReate Refferal | OnClick:<br>  Create Refferal:<br>    Show GrayBackground - Below Agent, Preview Panel<br>    Set Preview Panel state to New Refferal |
| 6 | Expand All | OnClick:<br>  Expand All:<br>    Set Clinical Info Pane state to All Expand |
| 7 | Collapse All | OnClick:<br>  Collapse All:<br><br>    Set Clinical Info Pane state to ClinicalInfoTabCollaped,<br>  Evaluation Panel state to Population Health Tab Collapsed,<br>  Evaluation Panel state to Population Health Tab Collapsed |
| 8 | Print | OnClick:<br>  Print Preview: |
| 9 | Filter | OnClick:<br>  Case 1 (If value of variable Filter equals "1"):<br>    Set value of variable Filter equal to "0"<br>    Set Filter to Default<br>  Case 2 (Else If value of variable Filter equals "0"):<br>    Set value of variable Filter equal to "1"<br>    Set Filter to Selected |

FIG. 4c

| Interactions |
|---|
| OnClick:<br>  Launch Problems CV: |
| OnClick:<br>  Launch Medications CV: |
| OnClick:<br>  Launch Launch CV |
| OnClick:<br>  Launch Allergies CV: |
| OnClick:<br>  Launch Documents CV: |
| OnClick:<br>  Expand Problems: |
| OnClick:<br>  Expand Medications: |
| OnClick:<br>  Collapsed Relevant Clinical Info: |
| OnClick:<br>  Expand Labs:<br>    Set Clinical Info Pane state to Lab Expanded |
| OnClick:<br>  Expand Documents:<br>    Set Clinical Info Pane state to Documents Expanded |
| OnClick:<br>  Expand Allergies:<br>    Set Clinical Info Pane state to Allergy Expanded |

FIG. 4d

FIG. 6a

| Not in my EHR | My EHR is not the source of the data |
| --- | --- |
| | My EHR is not a consumer of data from this source |
| New Since last Seen | The Data was Modified or New in the CDR since I last accessed the Clinical Viewer or the Open the SmartAgent. |
| | The idea of this rule is to use a timestamp (ADR/PLV?) that indicate when is the last time the user could have viewed the data in one of the HIES Applications. |
| | Last seen filter will be calculated per patient session. |
| Time filter | The Data meet timeframe criteria |

FIG. 6b

| | |
|---|---|
| Clinical Data | Eventually those rule typically should be flexible enough to be applied differently for each clinical Act type<br>a. Not my EHR<br>b. Not my EHR + Only last X month<br>c. Not my EHR + Only last X month + "New since Last Time Seen"<br>d. Not in My EHR + "New since Last Time Seen"<br>e. Only last X month<br>f. Only last X month + "New since Last Time Seen" |
| Recent Events (Working List) | a. Recent Events<br>b. Referrals |
| Populations Health | a. New Measure, Updated Measure (e.g. Diabetic Patient have new Measure<br>b. Alerts (an Alert available)<br>c. Reminders (Due date is soon) |
| Clinical Research | a. Candidate for Research |
| User Profile | a. Profile of the User is X |

FIG. 6c

| Functional Area | Use Case | Brief Description |
|---|---|---|
| Presentation | Present Patient Data | In this UC the system presents patient data to the user. The content and nature of the presentation is well defined in the mockup and requirements. |
| | Present Clinician Data | In this UC the system presents data from HIES that is not related to the patient viewed in the EHR. For example - "my recent events" from HIES Collaborate, "my admitted patients" and so on. Low priority |
| | Launch HIES Viewer | In this UC the system acts just as a entry point to the existing viewer (Clinical Viewer, Collaborate). The launch may or may not include context (user, patient, app).<br><br>For example - navigation menu for medications (even though no medication record is currently shown). |
| | Send To My EHR | In this UC the user selects act to be sent to his EHR and the system delivers them to the EHR to be presented there. |
| | Perform Search | In this UC the user searches for records within the patient record.<br>The search can either be on the codified data, or free search over text (notes within acts and the content of clinical documents). |
| | Control floating application state | e.g. Minimize, expand, size, position, dock, close etc. |

FIG. 7a

| Context Interception | Identify Application | In this UC the system intercepts the application (EHR) in which the user is using. For example - is the user working with Allscripts MyWay, Cerner etc. This context may be captured from the EHR screen or provided by the EHR.

Note - same application can be used for multiple instances. for example Cerner app is used in different "regions" in UPMC - Cerner H1, H2, H3. The instance must be used when applying content rules ("exclude mine", therfore, must solve this issue. |
|---|---|---|
| | Identify User | In this UC the system intercepts the user that is using the EHR in order for HIES to present data to that user, saccording to his security privelegds etc EHR side.

This context may be captured from the EHR screen or provided by the EHR.

There are several options here. |
| | Identify Patient | In this UC the system intercepts the patient that the user is currently looking at in the EHR. This context may be captured from the EHR screen or provided by the EHR. |
| | Identify Workflow Context | In this UC the system intercepts the workflow in which the user is at on the EHR side. For example - is the user on "labs" tab or on "medication" tab. This context may be captured from the EHR screen or provided by the EHR.

An advanced scenario here is responding to "free" selection on the screen, e.g. - user selects "Hgb" on the screen and we need to show history graph.

Priority is low |

FIG. 7b

| System Health | Monitor Service Health | In this UC the system need to monitor the server side of the applications. This may include standard monitoring services, performance counters etc.<br><br>Priority is medium |
|---|---|---|
| | Monitor Agents Health | In this UC the system monitors the scattered agents out there. For example - keep track of when each deployed agent has contacted, enable reporting (?).<br><br>the approach typically should be based on using calls made anyway by the agent rather than opening a dedicated channel for such monitoring. Another option is "report error" feature - either when the system fails, or when timeouts occur for example.<br><br>Priority is medium |
| Data Preparation | Prepare Patient Data for presentation | In this UC the system prepares data to be presented to the user. This includes fetching the data as well as filter out irrelevant records, based on rules.<br>In essence this is the area where VPO analyzer comes into play |
| | Apply Rules | Acting on patient data, the system decides which records are to be presented using rules.<br>It typically should be able to add more rules and yo adjust existing rules.<br>The rules currently known are:<br>- "exclude my EHR data"<br>- "exclude what I saw |

FIG. 7c

| | | |
|---|---|---|
| Configuration & Deployment | Install Agent on Citrix box | In this UC, setting up the agent is controlled by the customer IT personnel. For example by configuring Citrix sessions, or by network login script and so on. |
| | Install Agent on corporate box | In this UC, setting up the agent is controlled by the customer IT personnel. For example network login script and so on. |
| | Install Agent on Non-Corporate box | This UC describes how the system (agent) is installed on a non-corporate box, focusing in the community clinic. The assumption here is that the installer does not have significant deployment tools or skills. |
| | Deploy updates to Agent | In this UC the system needs to update to the agent applications scattered all over the network (and out of network for community clinics). |
| | Configure & Personalize presentation options | this includes (partial list):<br>- Presentations Skins Vs EHR<br>- Presentation rules<br>- Base query |
| Extension Developments | Develop & Configure Presentation Rules | |

FIG. 7d

| User Identifier | Patient Identifier | Last seen Timestamp |
|---|---|---|
| User 1 | Patient 1 | Datetime 1 |
| User 1 | Patient 2 | Datetime 2 |
| User 1 | Patient 3 | Datetime 3 |
| User 2 | Patient 4 | Datetime 4 |
| User 3 | Patient 5 | Datetime 5 |

FIG. 12

*Operations*

| Method | Notes | Parameters |
|---|---|---|
| BeginInterception() void Public | Called before the first field field is intercepted | char* [in] scenario<br><br>int [in] scenarioLen |
| InterceptField() void Public | Called as a relevant field has been intercepted | char* [in] scenario<br><br>int [in] scenarioLen<br><br>char* [in] fieldId<br><br>int [in] fieldIdLen<br><br>char* [in] interceptedValue<br><br>int [in] interceptedValueLen |
| EndInterception() void Public | Called after the last field in the scenario was intercepted | char* [in] scenario<br><br>int [in] scenarioLen |

FIG. 20

| Method | Notes | Parameters |
|---|---|---|
| CreateContextInterceptor()<br>IEHRContextInterceptor<br>Public | To be called when a new EHR window is discovered and so needs to be assigned with a context interceptor | int [in] applicationHandle<br><br>int [in] applicationType |
| CreatePositionInterceptor()<br>IEHRWindowStateInterceptor<br>Public | To be called when a new EHR window is discovered and so needs to be assigned with a context interceptor | int [in] applicationHandle<br><br>int [in] applicationType |
| CreateLaunchInterceptors()<br>IEHRLaunchIncerceptor[]<br>Public | to be called when the SmartAgent boots in order to "plant" the different launch interceptors for the different supported EHRs | |

FIG. 22

For each individual EMR within a first plurality of EMRs each interacting with an EMR community including a set of at least one EMR, performing a computerized context interception process using a processor to intercept context from the individual EMR and to identify therewithin an event whereby a health provider using said individual EMR calls up an individual patient's record from said individual EMR ⸺1830

Responsive to identification of said event, using a computerized output device for providing , to said health provider, patient record data pertaining to said individual patient and stored by a health information exchange system which stores patient record data regarding a multiplicity of patients ⸺1832

Using a processor to apply at least one predetermined rule involving intercepted EMR context and using a computerized output device to provide an alerting indication drawing the health provider's attention to at least some of said patient record data according to said predetermined rule. ⸺1834

FIG. 30

FACILITATING COMPUTERIZED INTERACTIONS WITH EMRS

REFERENCE TO CO-PENDING APPLICATIONS

The present application is a U.S. continuation patent application of, and claims priority under 35 U.S.C. § 120 to, U.S. nonprovisional patent application Ser. No. 13/208,417, filed Aug. 12, 2011, which '417 application published as U.S. patent application publication no. 2012/0215560, which '560 publication is incorporated herein by reference, and which '417 application is a U.S. continuation-in-part patent application of, and claims priority under 35 U.S.C. § 120 to, U.S. nonprovisional patent application Ser. No. 12/840,806, filed Jul. 21, 2010, which '806 application published as U.S. patent application publication no. 2011/0288877, which '877 publication is incorporated by reference herein, and the '417 application further is a U.S. nonprovisional patent application of, and claims priority under 35 U.S.C. § 119(e) to, U.S. provisional patent application Ser. No. 61/438,762, filed Feb. 2, 2011, which provisional patent application is incorporated by reference herein. Moreover, the disclosure of the priority patent document, namely the '762 application, is set forth in the Appendix hereto, which is incorporated by reference herein.

FIELD OF THE INVENTION

The present invention relates generally to systems for processing medical information and more particularly to computerized interactions with EMRs.

BACKGROUND OF THE INVENTION

Conventionally, information is transferred between an HIE and EMR via messages exchanged between the two systems. For example, an EMR may know how to import lab results from an HIES. An EMR may provide a tab in its main application, sometimes known as the "community tab" which enables a user to view, but not manipulate or import, HIE-provided information about a patient. Varying medical technology between the HIE and EMR, combined with a lack of ability to semantically resolve the variation, may impose limitations to these modes of information transfer.

According to Wikipedia, an Enterprise Master Patient Index (EMPI) is "a form of customer data integration (CDI) specific to the healthcare industry. Healthcare organizations or groups of them will implement EMPI to identify, match, merge, de-duplicate, and cleanse patient records to create a master index that may be used to obtain a complete and single view of a patient. The EMPI will create a unique identifier for each patient and maintain a mapping to the identifiers used in each record's respective system." It has been claimed that by using an EMPI for "correctly matching patient records from disparate systems and different organizations", it is possible to obtain "a complete view of a patient".

Known technologies relevant to the field of the invention include context management, single sign-on, CCOW or Screen capturing method for context interception.

Other state of the art health information exchange and integration systems, and conventional technology pertaining to certain embodiments of the present invention, are described in the following publications inter alia:
1. US20070118540
2. US20090125555
3. US20080189496
4. WO2007010485
5. JP6243152
6. DE10163469
7. US20040141661
8. US20090080408
9. US20040122709
10. US20040122719
11. US20040122787
12. US20040122707
13. Published US Application US20080046292;
14. Published US Application US20050144043; and
15. Published PCT Application WO/2007/084502.

Non-Patent Literature describing health information exchange through the use of semantic technology includes:
Comput Methods Programs Biomed., 2009, 93 (3), 297-312
XML technologies for the Omaha System: a data model, a Java tool and several case studies supporting home healthcare
Vittorini Pierpaolo; Tarquinio Antonietta; di Orio Ferdinando
Digital Society, 2009. ICDS '09. Third International Conference, 168-173
Semantic Exchange of Medicinal Data: A Way Towards Open Healthcare Systems
Puustjarvi, J and Puustjarvi, L
Engineering in Medicine and Biology Society, 2009. EMBC 2009. Annual International Conference of the IEEE, 1726-1729
Interoperability of personal health records
Lahteenmaki, Jaakko; Leppanen, Juha and Kaijanranta, Hannu
Information Technology: New Generations, 2009. ITNG '09. Sixth International Conference; 308-313
Healthcare Applications Interoperability through Implementation of HL7 Web Service Basic Profile
Hussain, M; Afzal, M; Ahmad, H. F; Khalid, N and Ali, A
Computer-Based Medical Systems, 2009. CBMS 2009. 22nd IEEE International Symposium; 1-6
Ontology-based approach to achieve semantic interoperability on exchanging and integrating information about the patient clinical evolution
Miyoshi, N, Ferreira, A and Felipe, J. C
Computer-Based Medical Systems, 2009. CBMS 2009. 22nd IEEE International Symposium; 1-6
Semantic biological image management and analysis
Chubb, C, Inagaki, Y, Cotman, C, Cummings, B and Sheu, P. C
Lähteenmäki, Jaakko, Leppänen, Juha, Kaijanranta, Hannu, "Interoperability of Personal Health Records" (2009) 31st Annual Int. Conference of the IEEE Engineering in Medicine and Biology Society, EMBC'09, Minneapolis, Minn., USA, 2-6 Sep. 2009, EMBC'09 DVD, 1726-1729.
Miyoshi, N. Ferreira, A. Felipe, J. C., "Ontology-based approach to achieve semantic interoperability on exchanging and integrating information about the patient clinical evolution", Computer-Based Medical Systems, 2009. CBMS 2009. 22nd IEEE International Symposium on Issue Date: 2-5 Aug. 2009 Healthcare Services Specification Project (HSSP) Service Functional Model (SFM) Specification—Decision Support Service (DSS), Version 1.0, Sep. 27, 2006, available on the World Wide Web.

The disclosures of all publications and patent documents mentioned in the specification, and of the publications and patent documents cited therein directly or indirectly, are hereby incorporated by reference.

SUMMARY OF THE INVENTION

Certain embodiments of the present invention seek to provide a technical solution for the problem of allowing medical data to be effectively retrieved, stored, and presented to medical service providing users where the medical data exists in digital form within a plethora of non-compatible, partially overlapping software systems which are constantly being updated.

Certain embodiments of the present invention seek to provide an interoperability solution for medical databases, providing a health information exchange system typically storing complete, single and harmonized patient records, and easing access thereto by bringing relevant information to a user at points in time in which that information is useful and as part of her or his workflows.

Certain embodiments of the present invention seek to bring relevant context-based information from inside the health information exchange system to a user e.g. physician's working environment and workflows (typically EMR), rather having the physician leave his working environment and search for the information he needs in a Clinical Viewer as an external application.

Certain embodiments of the present invention seek to enhance effective software compatibility including reducing dependency on EMR vendors to customize their software products in order to integrate with the health information exchange system platform (Button, Smart Access, and other services).

Certain embodiments of the present invention seek to provide easy and efficient access to specific context-based patient information eliminating the need to navigate through many patient's views in an external application.

Generally, Health Information Exchange (HIE) is defined as the mobilization of healthcare information electronically across organizations within a region, community or hospital system. HIE provides the capability to electronically move clinical information among disparate health care information systems while maintaining the meaning of the information being exchanged. The goal of HIE is to facilitate access to and retrieval of clinical data to provide safer, more timely, efficient, effective, equitable, patient-centered care. To meet this goal, HIE providers develop computerized infrastructures and applications that enable the information exchange and viewing of exchanged information. As HIE solutions complement the EMR applications, the EMR and HIE vendors are looking for ways to integrate with each other in order to enable:
1. Data exchange from the EMR the HIE and vice versa
2. Integrate the information hold in hold in the IHE within the EMR application and user workflow
3. Enrich EMR capabilities with the HIE solutions and services.

When an HIE solution is integrated with the EMR, both accessibility and User Context may be taken into account.

Certain embodiments of the present invention seek to provide an SOA-based platform that enables healthcare organizations and health information exchanges (HIEs) to integrate their information assets, through the creation of a virtual patient record by logically connecting a group of care providers and organizations without requiring the replacement of existing information systems. By providing ubiquitous access to integrated patient information, the solution virtually bridges gaps that often exist between inpatient/acute care and community care.

Typically, a single, virtual patient record contains complete and harmonized patient data by logically connecting a group of care providers and organizations without requiring the replacement of existing information systems. Smooth and easy access to the care-critical information stored in the HIE should be facilitated, by providing a user with relevant patient information at the point in time it is needed, as part of the clinical workflow.

The system shown and described herein may perform any or all of the above functionalities:

Provide important, relevant, context-based information from the HIE within a physicians' work environment and workflows (typically their EMRs)—as opposed to having the physicians leave their work environments and enter the HIE's Clinical Viewer functionality as an external application to search for the information needed.

Reduce the HIE's dependency on EMR vendors to customize their products in order to integrate with the HIE's platform (e.g. launch button, SSO, services).

Provide efficient access to specific context-based patient information, thereby eliminating the need to navigate through multiple clinical views in an external application such as a dbMotion Viewer.

The SmartAgent is a client application that is designed to meet the EMR users' need to get comprehensive and relevant clinical information on patients from sources of information which are not in their EMR, and in addition to serve as a gateway to HIE applications and solutions.

The client application, typically installed on the user's machine, is termed herein a SmartAgent client.

Examples of use scenarios include but are not limited to the following:

1. Smart Button within User, Patient and System Context: User opens a patient record in his EMR. SmartAgent, which is installed in his client machine, "captures" the patient identifier (MRN), the User Context (Username/Role) and the System context (SystemID) and calls a VPO Analyzer web service or Virtual Patient Object Clinical Data Web Service) that identifies the System, user and the patient. The user is authorized and the patient is found in the health information exchange system. The Client SmartAgent gets the response and presents a Floating Button. The Floating button includes Link to Launch Viewer with user and patient context. The User presses the button and seamlessly accesses the health information exchange system's Clinical Viewer.

2. VPO Analyzer attention rules: In order to bring more relevant information to the user, smart evaluations are typically provided on the VPO in the context of the user, patient and system. One of the Analyzer's attention rules may be "Exclude System Data" which excludes from the VPO Data that exists in the physician's own system. The response is "Clean" data excluding what a user can see in his EMR, which may be presented within the Results or Viewer Panes. The rule is typically constructed and operative to analyze the patient's clinical data and to alert the user in the SmartAgent client application that information that meets the rule exists and is available for viewing.

3. Semantic Search: A user may for example be looking for data on Diabetes in the health information exchange system. To do that he enables a search option in the floating toolbar and type the phrase "Dia". Search suggestions are presented and user selects the "Diabetes" Suggestion. As a result a "Results and Navigation" pane opens and presents the results for Diabetes from the Patient's VPO organized by Clinical Aspects (Medications, Problems, Population Membership, etc.). User presses "Diabetes" population and the Diabetes View is opened in the View panel.

4. Data Presentation and Launch Viewer: Any information found may be presented in a Data and Navigation Panel.

The information is organized according to the different clinical aspects (Laboratory, Medications, etc.) and evaluation aspects (Population membership, Metrics, Notifications, Alerts etc.). The clinical aspects and actual presented data may constitute a link to a relevant page in the health information exchange system's Clinical Viewer. The user can see under a Laboratory Results menu, a result for hbA1c from, say, a previous week. Aside from the result, 2 buttons may be provided, one to open the Laboratory Clinical View and another to open the Lab Result Page with the hbA1c history.

The present invention also typically includes at least the following embodiments:

a. A computerized system for supplying a human user with relevant, context-based patient information within the user's work environment and workflows.
b. A system according to embodiment a wherein the user's work environment includes at least one EMR.
c. A system according to embodiment b which does not require customization of the EMR.
d. A system according to embodiment 'a' which supplies information without requiring the user to navigate through multiple clinical views in an external application.
e. A system according to embodiment 'a' wherein the system includes a proactive apparatus which operates proactively, responsive to user context operations, to present relevant clinical information.
f. A system according to embodiment 'a' wherein the system includes a processor operative to select relevant information including performing a computerized analysis of a computerized patient record and deriving, from the analysis, relevant clinical information which is presented to the user, whereas other clinical information is not presented to the user.
g. A system according to embodiment 'f' wherein differentiation of relevant clinical information from other clinical information is based on at least one of the following: user context, profile, patient illness, ward context, EMR Workflow Context.
h. A system according to embodiment 'a' and wherein the system is operative to provide information, within the workflow, on overall patient events and evaluations for each individual physician or user.
i. A system according to embodiment 'a' and also comprising at least some aspects of a skin application shown and described herein.
j. A computerized method for supplying a human user with relevant, context-based patient information within the user's work environment and workflows.
k. A method according to embodiment 'j' wherein the user's work environment includes at least one EMR.
l. A method according to embodiment 'k' which does not require customization of the EMR.
m. A method according to embodiment 'j' which supplies information without requiring the user to navigate through multiple clinical views in an external application.
n. A method according to embodiment 'j' wherein the method includes a proactive apparatus which operates proactively, responsive to user context operations, to present relevant clinical information.
o. A method according to embodiment 'j' wherein the method includes a processor operative to select relevant information including performing a computerized analysis of a computerized patient record and deriving, from the analysis, relevant clinical information which is presented to the user, whereas other clinical information is not presented to the user.
p. A method according to embodiment 'o' wherein differentiation of relevant clinical information from other clinical information is based on at least one of the following: user context, profile, patient illness, ward context, EMR Workflow Context.
q. A method according to embodiment 'a' and wherein the system is operative to provide information, within the workflow, on overall patient events and evaluations for each individual physician or user.
r. A method according to embodiment 'j' and also comprising at least some aspects of a skin application shown and described herein.
s. A computer program product, comprising a computer usable medium having a computer readable program code embodied therein, the computer readable program code adapted to be executed to implement any of the methods shown and described herein.

Certain embodiments of the present invention seek to provide a decision making system including a system of logic including hierarchical semantic relationships, a plurality of systems of medical information which are provided in a plurality of local terminologies respectively, and a decision making apparatus for transforming the medical information in the local terminologies to transformed information usable by the system of logic and for using the system of logic to make at least one decision based on the transformed information, without translating the system of logic into the plurality of local terminologies. The term "terminology" is intended to include any scheme for representing medical information. The following terms and other terms defined herein may be construed either in accordance with any definition thereof appearing in the prior art literature or in accordance with the specification, or as follows:

Classification Type—A base set of classifications which all others derive from. The existing classifications are:
Candidate—represents a new population element entering the system.
ActiveMember—represents a member of the population currently being monitored
DormantMember—represents a member who is "sleeping" or currently active but not being monitored (in a dormant state)
Evaluation Task—an evaluation task combines a set of executable rules, an evaluation goal, activation, and a set of triggering rule subscriptions. When a member is associated with a task (by having a specific classification) the triggering rule subscriptions are sent to the Data Event Monitor for that member. When task processing is activated, if that member has had any matching triggering rules fire, the task is sent to be processed (along with the member details).
Member—The population element of a specific Guard, each member is tagged with its population source and contains a list of classifications.
Member Classification—Guard evaluation tasks are grouped by classifications.
If a member belongs to a specific classification, that member has certain tasks associated with him or her.
Population Source—the source of members for the Guard, could be an external list, an enrollment service, or a data event monitor.
Triggering Rule Subscription—subscription for the Abstract Rule Monitor, contains a Pattern Rule Identifier and a set of subscription arguments.
Schedule—an alarm (scheduled or event based) used to activate processing for a particular evaluation task (or set of evaluation tasks).

DEM—data event monitor e.g. as described herein
EMPI—Conventional Enterprise Master Patient Index service
Principal Index—aka (also termed herein) Leading Index
VIA—a commercial Virtual Identity Aggregation service provided by DBMotion Inc., Israel
ACEI—angiotensin-converting enzyme inhibitors
LVS—Left Ventricular Systolic
LVSD—Left Ventricular Systolic Dysfunction
DBMotion—refers to a functionality which is either commercially available from DBMotion Inc., Israel and/or is shown and described herein. Other definitions, acronyms, and abbreviations useful in understanding certain embodiments of the present invention, are provided in the table of FIG. 2 of incorporated U.S. patent application publication no. 2012/0215560.

In accordance with an aspect of the invention, there is provided a health information exchange system comprising an apparatus for archiving health information using a health information encoding procedure only if the health information fulfills a criterion of frequent use; and an apparatus for using a first procedure to respond to queries pertaining to the health information which fulfills the criterion of frequent use and using a second procedure to respond to queries not pertaining to the health information which fulfills the criterion of frequent use.

In accordance with an aspect of the invention, there is further provided a health information exchange system comprising an ontological apparatus for defining and storing ontological link elements ontologically linking between individual health care information items within a first population of health care information items; an apparatus for receiving a second population of health care information items and for associating at least some individual items in the second population, with corresponding individual items within the first population of health care information items; and an apparatus for responding to queries regarding particular information items in the second population including translating the particular information items into items in the first population corresponding to the particular information items and using link elements linking the items in the first population corresponding to the particular information items to generate data pertaining to the particular information items in the second population.

In accordance with an embodiment of the invention, there is provided a system comprising an apparatus for making at least one health decision based on the queries.

In accordance with an embodiment of the invention, there is further provided a system also comprising apparatus for implementing the at least one health decision.

In accordance with an embodiment of the invention, there is further provided a system also comprising apparatus for making at least one health decision based on the queries.

In accordance with an embodiment of the invention, there is further provided a system also comprising apparatus for implementing the at least one health decision.

In accordance with an aspect of the invention, there is provided a health information exchange method comprising archiving health information using a health information encoding procedure only if the health information fulfills a criterion of frequent use; and using a first procedure to respond to queries pertaining to the health information which fulfills the criterion of frequent use and using a second procedure to respond to queries not pertaining to the health information which fulfills the criterion of frequent use. In accordance with an aspect of the invention, there is provided a health information exchange method comprising defining and storing link elements linking between individual health care information items within a first population of health care information items; receiving a second population of health care information items and associating at least some individual items in the second population, with corresponding individual items within the first population of health care information items; and responding to queries regarding particular information items in the second population including translating the particular information items into items in the first population corresponding to the particular information items and using link elements linking the items in the first population corresponding to the particular information items to generate data pertaining to the particular information items in the second population.

In accordance with an embodiment of the invention, there is further provided a method also comprising making at least one health decision based on the queries.

In accordance with an embodiment of the invention, there is still further provided a method also comprising implementing the at least one health decision.

In accordance with an embodiment of the invention, there is yet further provided a method also comprising making at least one health decision based on the queries.

In accordance with an embodiment of the invention, there is yet further provided a method also comprising implementing the at least one health decision.

In accordance with an aspect of the invention, there is provided a computer program product, comprising a computer usable medium having a computer readable program code embodied therein, the computer readable program code adapted to be executed to implement a health information exchange method comprising archiving health information using a health information encoding procedure only if the health information fulfills a criterion of frequent use; and using a first procedure to respond to queries pertaining to the health information which fulfills the criterion of frequent use and using a second procedure to respond to queries not pertaining to the health information which fulfills the criterion of frequent use.

In accordance with an aspect of the invention, there is yet further provided a computer program product, comprising a computer usable medium having a computer readable program code embodied therein, the computer readable program code adapted to be executed to implement a health information exchange method comprising defining and storing link elements linking between individual health care information items within a first population of health care information items; receiving a second population of health care information items and for associating at least some individual items in the second population, with corresponding individual items within the first population of health care information items; and responding to queries regarding particular information items in the second population including translating the particular information items into items in the first population corresponding to the particular information items and using link elements linking the items in the first population corresponding to the particular information items to generate data pertaining to the particular information items in the second population.

In accordance with an embodiment of the invention, there is yet further provided a computer program product wherein the method also comprises making at least one health decision based on the queries.

In accordance with an embodiment of the invention, there is yet further provided a computer program product wherein the method also comprises implementing the at least one health decision.

In accordance with an embodiment of the invention, there is yet further provided a computer program product wherein the method also comprises making at least one health decision based on the queries.

In accordance with an embodiment of the invention, there is yet further provided a computer program product wherein the method also comprises implementing the at least one health decision.

In accordance with an embodiment of the invention, there is yet further provided a method wherein the second population of health care information items are expressed in a local terminology and are mapped to a baseline terminology in which the first population of health care information items are expressed, to enable terminology interoperability at least when responding to queries.

In accordance with an embodiment of the invention, there is yet further provided a method wherein the baseline terminology is semantically enriched by associating semantic information therewith, the method also comprising generating conclusions about health information expressed in at least one local terminology by using the semantic information rather than by defining semantic relations for the local terminology.

In accordance with an embodiment of the invention, there is yet further provided a system in which only a subset of a universe of health information is archived.

In accordance with an embodiment of the invention, there is yet further provided a system wherein the apparatus for responding to queries uses a first procedure to respond to queries pertaining to the subset and uses a second procedure to respond to queries not pertaining to the universe of health information but not pertaining to the subset.

In accordance with an embodiment of the invention, there is yet further provided a system also including an end user interface allowing end users to define rules; and a decision support subsystem (DSS) interacting with the end user interface and using semantic capabilities of a baseline terminology in which the first population of health information items is encoded, to simplify definition of rules by the end users.

In accordance with an embodiment of the invention, there is yet further provided a system wherein the decision support subsystem comprises an Enterprise DSS which has a process cycle and which uses DSS rules to define all phases in the process cycle.

In accordance with an embodiment of the invention, there is yet further provided a method wherein the translating and the using is applied to a use case involving processing of Smart Guard Adapters, the processing including at least one of developing, defining and configuring.

In accordance with an embodiment of the invention, there is yet further provided a method wherein the translating and the using is applied to a use case involving a SmartWatch System, the use case including at least one of processing and monitoring health of the system.

In accordance with an embodiment of the invention, there is yet further provided a method wherein the translating and the using are applied to a use case involving Managing Guard runtime.

In accordance with an embodiment of the invention, there is yet further provided a method wherein the translating and the using are applied to a use case involving applying Guard changes.

In accordance with an embodiment of the invention, there is yet further provided a method wherein the translating and the using are applied to a use case involving task activation based upon a schedule.

In accordance with an embodiment of the invention, there is yet further provided a method wherein the translating and the using is applied to a use case involving identifying patients to be added to a defined population of patients.

In accordance with an embodiment of the invention, there is yet further provided a method wherein the translating and the using are applied to a use case involving monitoring a population of patients including determining if they need to be evaluated, evaluating them thereby to generate at least one evaluation result, and responding to the evaluation result.

In accordance with an embodiment of the invention, there is yet further provided a method wherein the health information encoding procedure includes mapping health information expressed in at least one local terminology to a baseline terminology to enable terminology interoperability and storing ontological information interrelating health information items expressed in the baseline terminology.

In accordance with an embodiment of the invention, there is yet further provided a system wherein the ontological apparatus includes interrelationships between clinical-level information items.

In accordance with an embodiment of the invention, there is yet further provided a system wherein the clinical-level information item comprises at least one health care information item specifying at least one of a disease, rather than only a class thereof, and a medication, rather than only a class thereof, such as "Left Ventricular Heart Failure", rather than "Cardio-vascular disorder", and "Amoxicillin 250 MG Oral Capsule [Amoxymed]", rather than "Antibiotic", respectively.

In accordance with an embodiment of the invention, there is yet further provided a system wherein the ontological apparatus maps at least one legacy concept expressed in local terminology to at least one ontology concept expressed in a baseline terminology thereby allowing queries on the level of a single legacy concept to be responded to, for example, the following legacy concept: (System: ICD9, Code: 428.9, Designation: HEART FAILURE NOS) may be mapped to the following Ontology concept: (System: SNOMED-CT; Code: 84114007; Designation: Heart failure (disorder). Very generic examples of classifications are "Disorder", "Medicine", "Procedure"; more specific classification examples are "Cardio-vascular disorder", "Antibiotics" etc. Classifications do not identify a patient's clinical status; for example, it is not enough to say in a clinical record that the patient has "Cardio-vascular disorder" as there are many types of such disorders, and it is typically useful to know which disorder the patient suffers from, to decide how to treat it. Examples of clinical-level information items are "Left Ventricular Heart Failure", "Amoxicillin 250 MG Oral Capsule [Amoxymed]"; these information items are sufficiently detailed to describe aspects of an individual patient's clinical status and/or treatment rather than mere classifications thereof.

Also provided is a computer program product, comprising a typically non-transitory computer usable medium or computer readable storage medium, typically tangible, having a computer readable program code embodied therein, said computer readable program code adapted to be executed to implement any or all of the methods shown and described herein. It is appreciated that any or all of the computational steps shown and described herein may be computer-implemented. The operations in accordance with the teachings herein may be performed by a computer specially constructed for the desired purposes or by a general purpose computer specially configured for the desired purpose by a computer program stored in a typically non-transitory computer readable storage medium.

Any suitable processor, display and input means may be used to process, display e.g. on a computer screen or other computer output device, store, and accept information such as information used by or generated by any of the methods and apparatus shown and described herein; the above processor, display and input means including computer programs, in accordance with some or all of the embodiments of the present invention. Any or all functionalities of the invention shown and described herein may be performed by a conventional personal computer processor, workstation or other programmable device or computer or electronic computing device, either general-purpose or specifically constructed, used for processing; a computer display screen and/or printer and/or speaker for displaying; machine-readable memory such as optical disks, CDROMs, magnetic-optical discs or other discs; RAMs, ROMs, EPROMs, EEPROMs, magnetic or optical or other cards, for storing, and keyboard or mouse for accepting. The term "process" as used above is intended to include any type of computation or manipulation or transformation of data represented as physical, e.g. electronic, phenomena which may occur or reside e.g. within registers and/or memories of a computer. The term processor includes a single processing unit or a plurality of distributed or remote such units.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may wherever suitable operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

Elements separately listed herein need not be distinct components and alternatively may be the same structure.

Any suitable input device, such as but not limited to a sensor, may be used to generate or otherwise provide information received by the apparatus and methods shown and described herein. Any suitable output device or display may be used to display or output information generated by the apparatus and methods shown and described herein. Any suitable processor may be employed to compute or generate information as described herein e.g. by providing one or more modules in the processor to perform functionalities described herein. Any suitable computerized data storage e.g. computer memory may be used to store information received by or generated by the systems shown and described herein. Functionalities shown and described herein may be divided between a server computer and a plurality of client computers. These or any other computerized components shown and described herein may communicate between themselves via a suitable computer network.

With regard to drawings and detailed descriptions of embodiments and examples of the present invention, certain embodiments of the present invention are illustrated and described in detail in the incorporated patent publication of the priority document, namely U.S. Patent Application Publication No. 2012/0215560, to which reference is now made as if such disclosure were set forth next herein.

BRIEF DESCRIPTION OF THE DRAWINGS

Certain embodiments of the present invention are illustrated in the following drawings:

FIG. 1b is a table summarizing an example set of functional requirements of a content/VPO analyzer included in the apparatus shown and described herein.

FIG. 1c is a table summarizing an example set of functional requirements of a content capturing and sharing functionality included in the apparatus shown and described herein.

FIG. 1d is a table summarizing an example set of functional requirements of a semantic search functionality included in the apparatus shown and described herein.

FIG. 1e is a table summarizing an example set of functional requirements of a floating application included in the apparatus shown and described herein.

FIG. 2a is a table summarizing an example set of non-functional auditing, security and localization requirements of apparatus shown and described herein.

FIG. 2b is a table summarizing an example set of non-functional topological and pre-requisite requirements of the apparatus shown and described herein.

FIG. 2c is a table summarizing an example set of non-functional performance requirements of apparatus shown and described herein.

FIG. 2d is a table summarizing an example set of non-functional reusability and integrability requirements of the apparatus shown and described herein.

FIG. 3b is a simplified pictorial illustration of an example user interface for a FloatingClosed functionality.

FIG. 3c is an example object table useful in understanding the functionality of the user interface of FIG. 3b.

FIG. 3d is a simplified pictorial illustration of an example user interface for a FloatingSearchOpen functionality.

FIG. 4c is an example object table useful in understanding the functionality of the user interface of FIG. 157b.

FIG. 4d is an example Object Table.

FIG. 6a is a simplified pictorial illustration of an example method for highlighting of the background of a patient's name field.

FIG. 6b is a table presenting an example set of basic rules.

FIG. 6c is a table presenting an example set of rule combinations.

FIG. 7a is a table of an example set of presentation use cases.

FIG. 7b is a table of an example set of context interception use cases.

FIG. 7c is a table of an example set of system health use cases.

FIG. 7d is a table of an example set of data preparation, configuration & deployment, and extension development use cases.

FIGS. 9, 10a-10c, 11-13 present an example use case model useful in conjunction with the system of FIG. 1a.

FIG. 12 is an example table suitable for storing a timestamp per user and per patient according to certain embodiments.

FIG. 20 is a table of the InterceptionEventDispatcher's operations according to certain embodiments.

FIG. 22 is a table of Operations, some or all of which may be performed by the InterceptorsFactory functionality of FIG. 21.

FIG. 24 is a diagram of example Framework and Contracts pertaining to the VPOAnalyzer of FIG. 1a.

FIG. 30 is a top-level simplified flowchart illustration of a method of operation for the smart agent system of FIG. 1a, according to an embodiment of the present invention.

DETAILED DESCRIPTION OF CERTAIN EMBODIMENTS

Figure 1A:
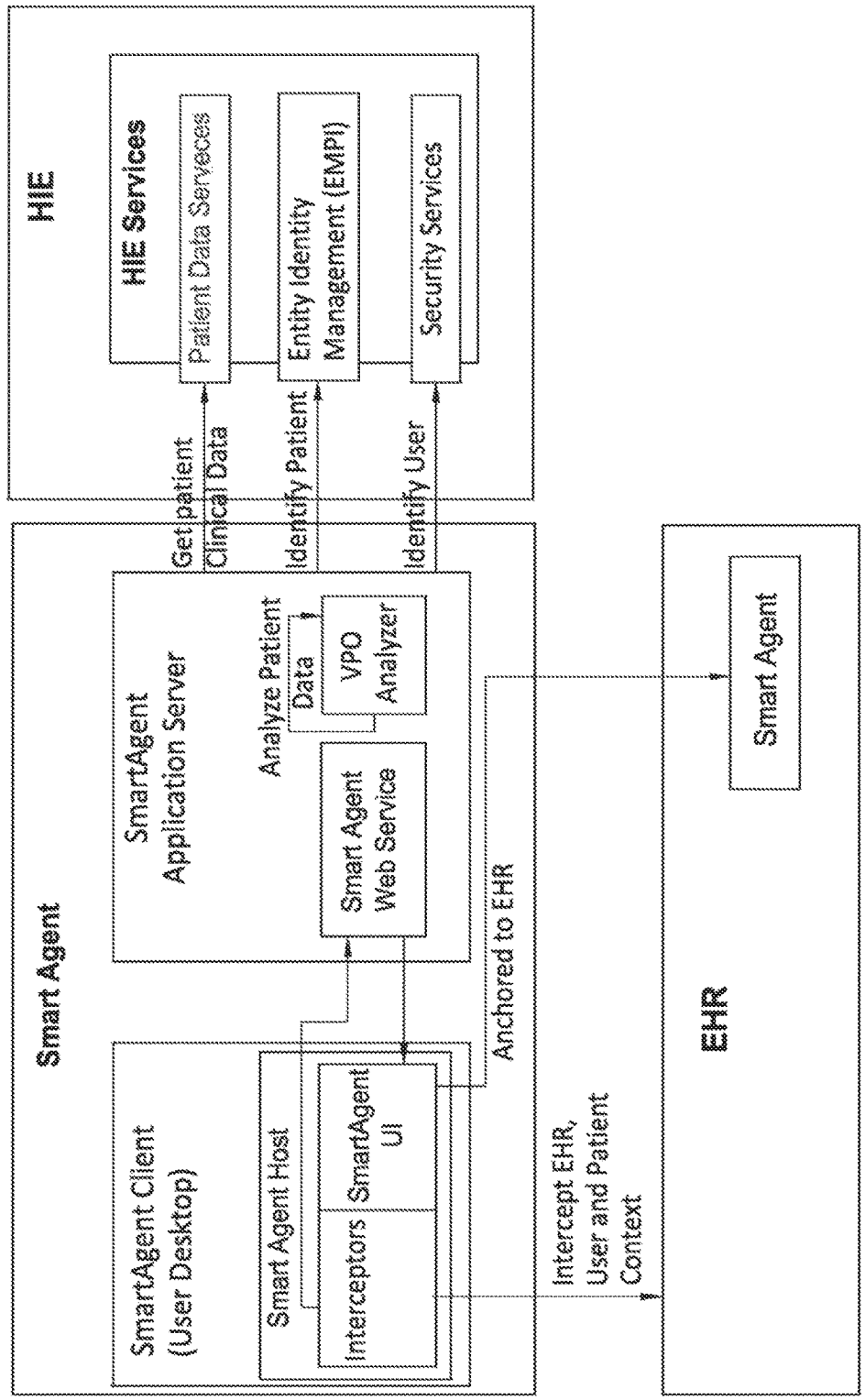
FIG. 1a is a simplified functional block diagram of a high level architecture of a smart agent system constructed and operative in accordance with certain embodiments of the present invention.

FIG. 1a is a simplified functional block diagram of a high level architecture of a smart agent system constructed and operative in accordance with certain embodiments of the present invention. In FIG. 1a, it is appreciated that EMR is also termed EHR herein. Data Analyzer Desktop Agent is also termed EHR Agent Host or SmartAgent host herein. Agent Viewer is also termed EHR Agent User Interface or SmartAgent user interface herein. A VPO (Virtual Patient Object) is an Object, in the sense of object-oriented programming, that is retrieved by a Patient data services functionality and stores a patient's clinical History. A VPO Analyzer is also termed EHR Agent Orchestration Web Service herein. A VPO Business Domain is also termed Clinical Data Web Service or "Patient Clinical Data Services" or "Patient data services" herein. The term "WPF" refers to a conventional computer-software graphical subsystem for rendering user interfaces such as but not limited to, for Windows-based applications, Windows Presentation Foundation.

Figure 19:
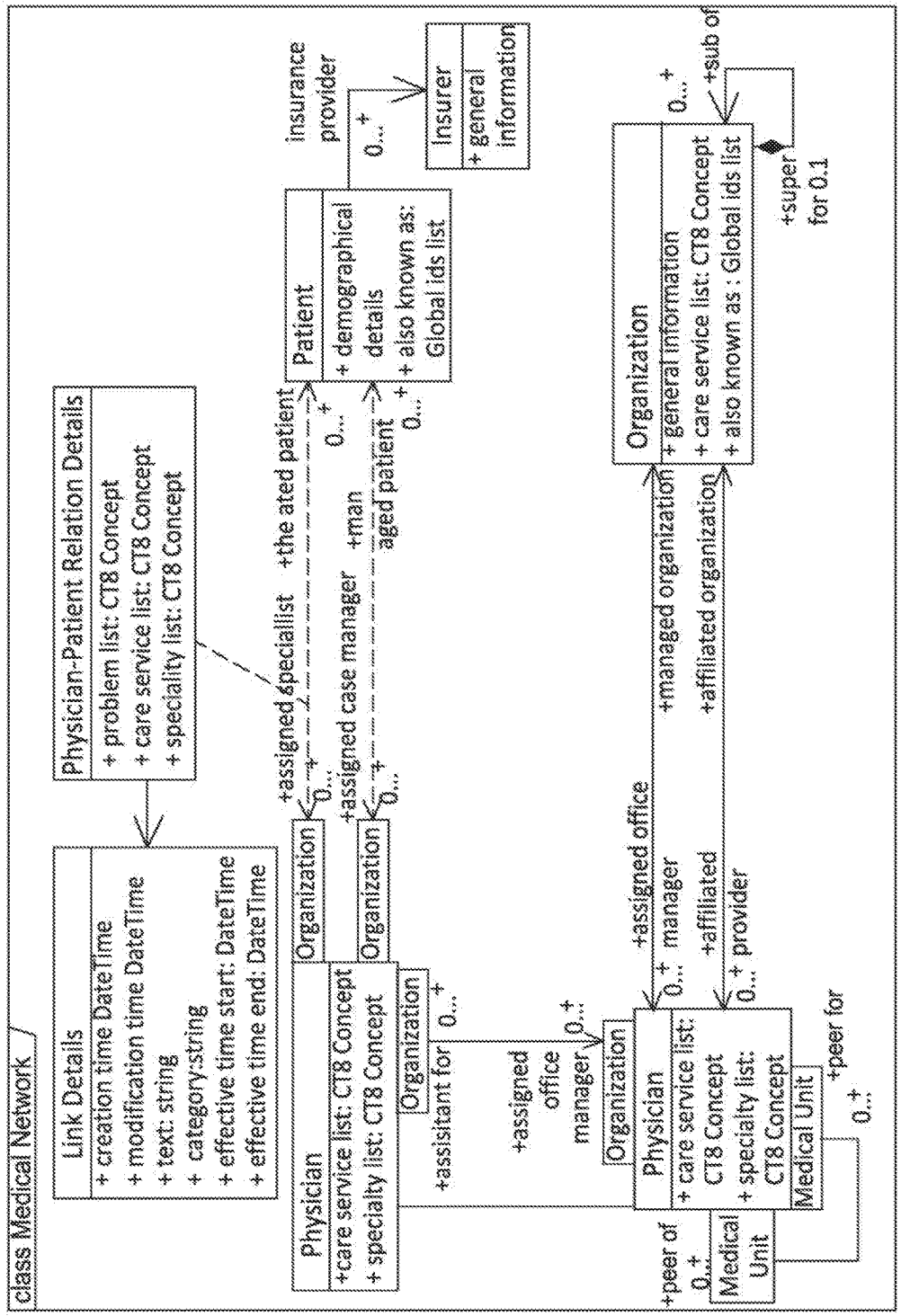
FIG. 19 is a pictorial diagram of a medical domain comprising an interconnected network of entities according to certain embodiments.

The term "PPOL" refers to a Patient-Provider-Organization Link such as but not limited to that provided in DBMotion's commercially available HIE. Generally, a medical domain typically comprises interconnected network of entities (e.g. as shown in FIG. 19) such as Providers (e.g., medical staff, clinician, nurse) providing care services to Patients, at medical Organizations (e.g., clinic, hospital). The information about relations (Links) between medical entities is an integral part of healthcare information which facilitates intelligent services. For example, a PPOL may list patients being treated by a specific clinician, describe an organizational hierarchy of a medical unit, and return the PCP of a specific patient. A Providers-Patients-Organizations Link (PPOL) computerized service typically provides and manipulates information about relations (Links) between medical entities. A PPOL typically manages different entities and the relations between the entities in the medical domain, such as—for example—relationships between a patient's GP and the physician's office manager. A PPOL typically does one or more of: connects to a conventional EMPI (Enterprise Master Patient Index) patient registry; provides a unique ID for patient and provider identities (aka cluster); stores provider-provider relations, e.g. office manager; stores provider-patient relations, e.g. PCP based on ADT messages; and acts as a providers' registry or connects to an existing such registry.

The smart agent system of FIG. 1a typically includes a client and a server, each including some or all of the illustrated blocks, interacting suitably e.g. as shown. The SmartAgent client application typically intercepts EMR activities and recognizes EMR context e.g. user, patient and workflow e.g. as described herein in detail. The PPOL module typically performs identity management including harmonization of different identifiers of entities. The CTS terminologies and vocabularies module typically harmonizes local terminologies used in various data sources to the ontology used by the HIES e.g. the HIES commercially available from DbMotion, Israel. The security authority block typically authenticates and authorizes user access to patients' clinical data. The "get VPO" block typically retrieves patient data (e.g. VPOs—virtual patient objects) from repositories, which may be harmonized and/or federated, in the HIES.

The term "smart agent" is used herein to include an HIES-EMR bridging system according to any of the embodiments shown and described herein, which facilitates cooperation between HIES and a population of one or more EMRs with which the HIES interacts. For example, the smart agent may perform any or all of the following operations:

a. identify an application which has opened on a work station on which the HIES client is installed, as a medical service provider application e.g. EMR. This may occur because the EMR is compatible with a context sharing standard that the smart agent also supports or may be screen captured. Alternatively, APIs in the operating system may be available which define (assign an operating system name to) the relevant screen and/or fields within the screen, enabling the smart agent to identify the application.

b. identify health care providing user e.g. because user logins in with password, or by capturing user's name from the screen, or e.g. authenticating the user using single-sign on functionality.

c. assuming that the EMR is currently working on the medical record of a particular patient, the smart agent may find the patient identifier, e.g. by screen capture or by context sharing. Typically, when an EMR enters a medical record, the smart agent retrieves the patient identifier by first recognizing the EMR page through which the patient user accesses the medical records and then, e.g. using prior knowledge re the location of the patient identifier on that page, capturing the user identifier.

d. optionally, filter available HIES information, e.g. using suitable "attention rules", to select suitable information to provide to the user identified in (b), pertaining to the patient identified in (c). Typically, attention rules filter out either irrelevant information or superfluous (repetitive) information, or both.

e. display all, or some (as filtered in (d)) information pertaining to the patient identified in (c.). Typically, all information available from all EMRs with which the HIES interacts, is available to be displayed, unless filtered. Typically, this information is displayed to the health care providing user via an HIE data importer such as a tab or button that takes the user to an HIE portal.

Examples of the operation of steps (d) and (e):

(i) if the user presses on the lab page in her or his EMR, the lab page may be identified by the hovering smart agent. The smart agent may then display to the user only lab results which are not present in her EMR, optionally blinking to indicate that such exist and are available for viewing.

(ii) if the user presses on a medicine page in her or his EMR, the hovering smart agent may intercept that the user is prescribing penicillin to a patient called Susan Smith and may then display only relevant information such as all allergies known for Susan Smith, or the subset of Susan Smith allergies pertinent to penicillin.

(iii) The user presses on a lab result page and sends Susan Smith to do a lab test. The smart agent may intercept this and blink or otherwise indicate that Susan has already done this lab test.

The SmartAgent user interface and behavior is designed to be floated on top of an instance of an EMR and not to interrupt the regular user workflow.

Figure 3A:
FIG. 3a is an example user interface useful in entering a patient file and launching the SmartAgent system provided according to certain embodiments of the present invention, including an example of how a smart agent may position itself vis a vis an EHR according to certain embodiments.

A Floating application within User, Patient and System Context, e.g. as shown in FIG. 3a, may be used as follows:
1. The User opens a patient record in the EMR.
2. A HIES client agent (SmartAgent) installed on the client machine "captures" the patient identifier (MRN), the User Context (Username/Role), and the System Context (SystemID) and calls the HIE's VPO Analyzer web service, which identifies the System, the User and the Patient.
3. The User is authorized and the Patient is found in the HIE.
4. The client SmartAgent gets the response and presents a Floating Application. The Floating button includes a link to launch the HIE's Viewer with the user and patient context.
5. The User clicks the button and seamlessly accesses the HIE's Clinical Viewer.

The VPO (Virtual Patient Object) Analyzer of FIG. 1a typically performs smart evaluations on the VPO in the context of the User, the Patient and the System, in order to provide more relevant and needed information to the User. One of the VPO Analyzer's methods is "Exclude System Data". This method excludes data from the VPO that already exists in the User's EMR. This results in "clean" data (excluding what user can already see in the EMR) that is presented within the Results or Viewer Panes.

A Semantic Search method is now described:

1. The user looks for data on Diabetes (say) in the HIES. To do so, the User enables the Search option in the floating toolbar and types the phrase "Dia".
2. Search suggestions are presented and user selects the "Diabetes" Suggestion.
3. As a result, the Results and Navigation pane opens and presents the results for Diabetes from the Patient's VPO, organized according to Clinical Aspects (Medications, Problems, Population Membership, etc).
4. The User clicks the "Diabetes" population.
5. The Diabetes View is opened in the View panel.

A process operative to Launch an HIES Viewer and CareBoard is now described. Any information found is presented in the Data and Navigation panel. The information is organized according to the different clinical aspects (Laboratory, Medications, etc.) and evaluation aspects (Population membership, Metrics, Notifications, Alerts etc.). The clinical aspects and actual presented data are links to the relevant page in the HIES's Clinical Viewer or Collaborate. Example: Under the Lab Results menu, the user sees a result for hbA1c from last week. Beside the result there are two buttons: one opens the Labs Clinical View and the other opens the Lab Results Page with the hbA1c history.

FIG. 1b is a table summarizing an example set of functional requirements of a content/VPO analyzer included in the apparatus shown and described herein.

FIG. 1c is a table summarizing an example set of functional requirements of a content capturing and sharing functionality included in the apparatus shown and described herein.

FIG. 1d is a table summarizing an example set of functional requirements of a semantic search functionality included in the apparatus shown and described herein.

FIG. 1e is a table summarizing an example set of functional requirements of a floating application included in the apparatus shown and described herein.

FIG. 2a is a table summarizing an example set of non-functional auditing, security and localization requirements of apparatus shown and described herein.

FIG. 2b is a table summarizing an example set of non-functional topological and pre-requisite requirements of apparatus shown and described herein.

FIG. 2c is a table summarizing an example set of non-functional performance requirements of apparatus shown and described herein.

FIG. 2d is a table summarizing an example set of non-functional reusability and integrability requirements of apparatus shown and described herein.

In an OnPageLoad mode of operation, FIG. 3a is an example user interface useful in entering a Patient File and launching the SmartAgent system provided according to certain embodiments of the present invention.

Floating Application Small Panel: An example user interface for a FloatingClosed functionality is illustrated in FIG. 3b. An example object table useful in understanding the functionality of the user interface of FIG. 3b is illustrated in FIG. 3c. Footnotes in the first column of the object table of FIG. 3c refer to suitably marked locations in the user interface of FIG. 3b, respectively.

An example user interface for a FloatingSearchOpen functionality is illustrated in FIG. 3d.

Figure 4A:
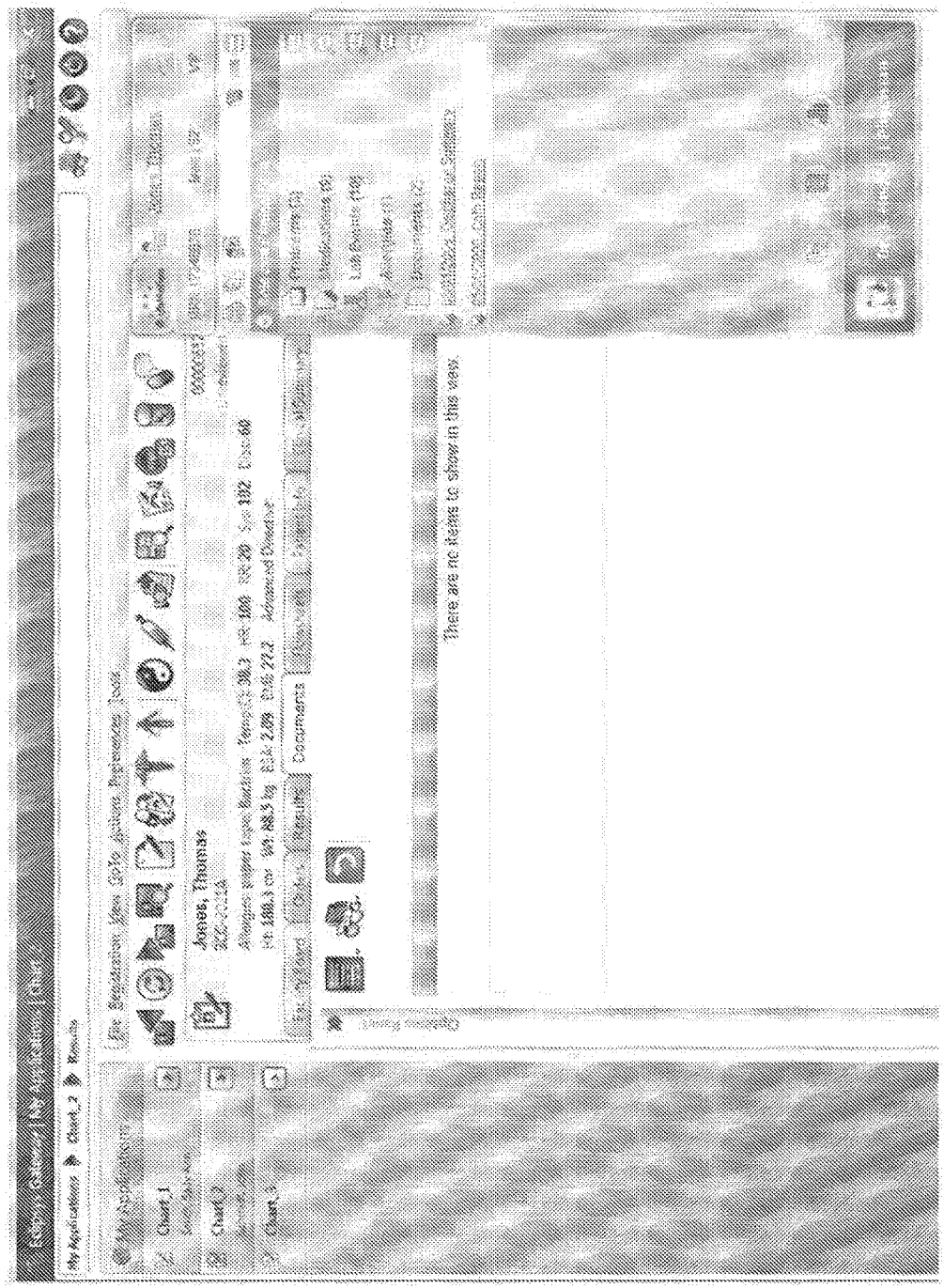
FIG. 4a illustrates the SmartAgent application, according to certain embodiments of the present invention, hovering on top of an example EMR (Allscripts Sunrise—commercially available EMR) in an expanded mode, e.g. by presenting the smart agent's clinical data on top of the EMR e.g. as described herein with reference to FIGS. 3a-3c.

FIG. 4a illustrates the SmartAgent application hovering on top of an example EMR (Allscripts Sunrise—commercially available EMR) in an expanded mode.

Figure 4B:
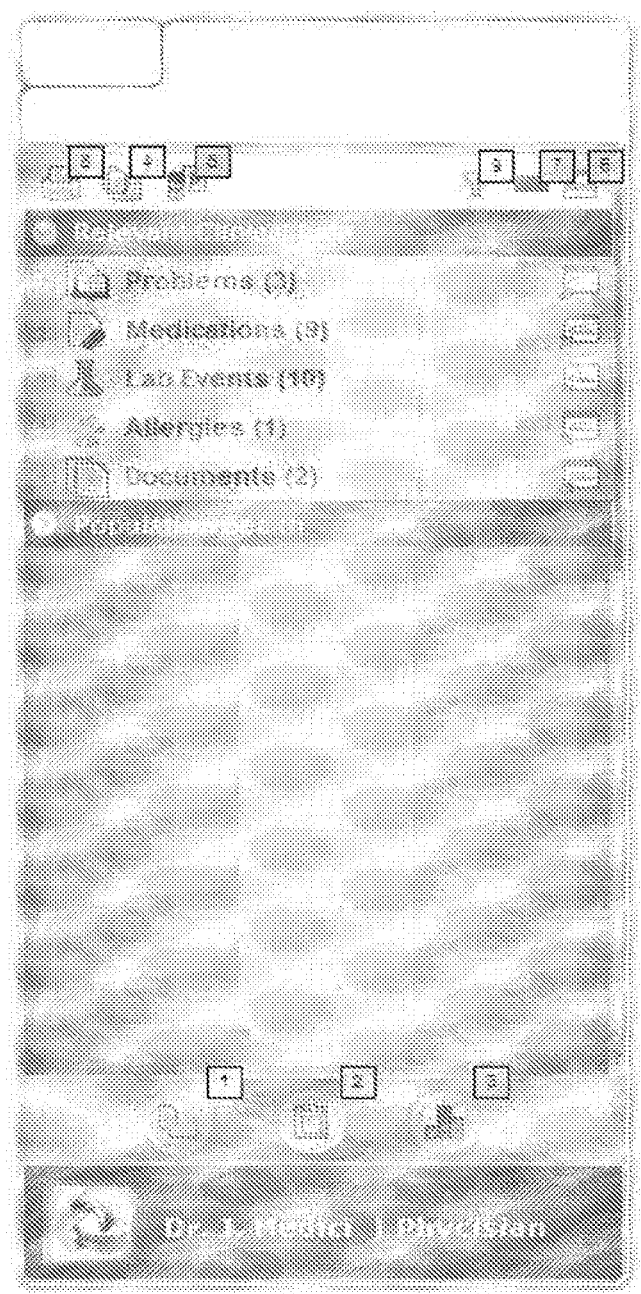
FIG. 4b is an enlarged view of the expanded SmartAgent panel, according to certain embodiments of the present invention.

FIG. 4b is an enlarged view of the expanded SmartAgent panel.

An example object table useful in understanding the functionality of the user interface of FIG. 4b is illustrated in FIG. 4c. Footnotes in the first column of the object table of FIG. 4c refer to suitably marked locations in the user interface of FIG. 4b, respectively.

FIG. 4d is an Object Table.

Figure 5:
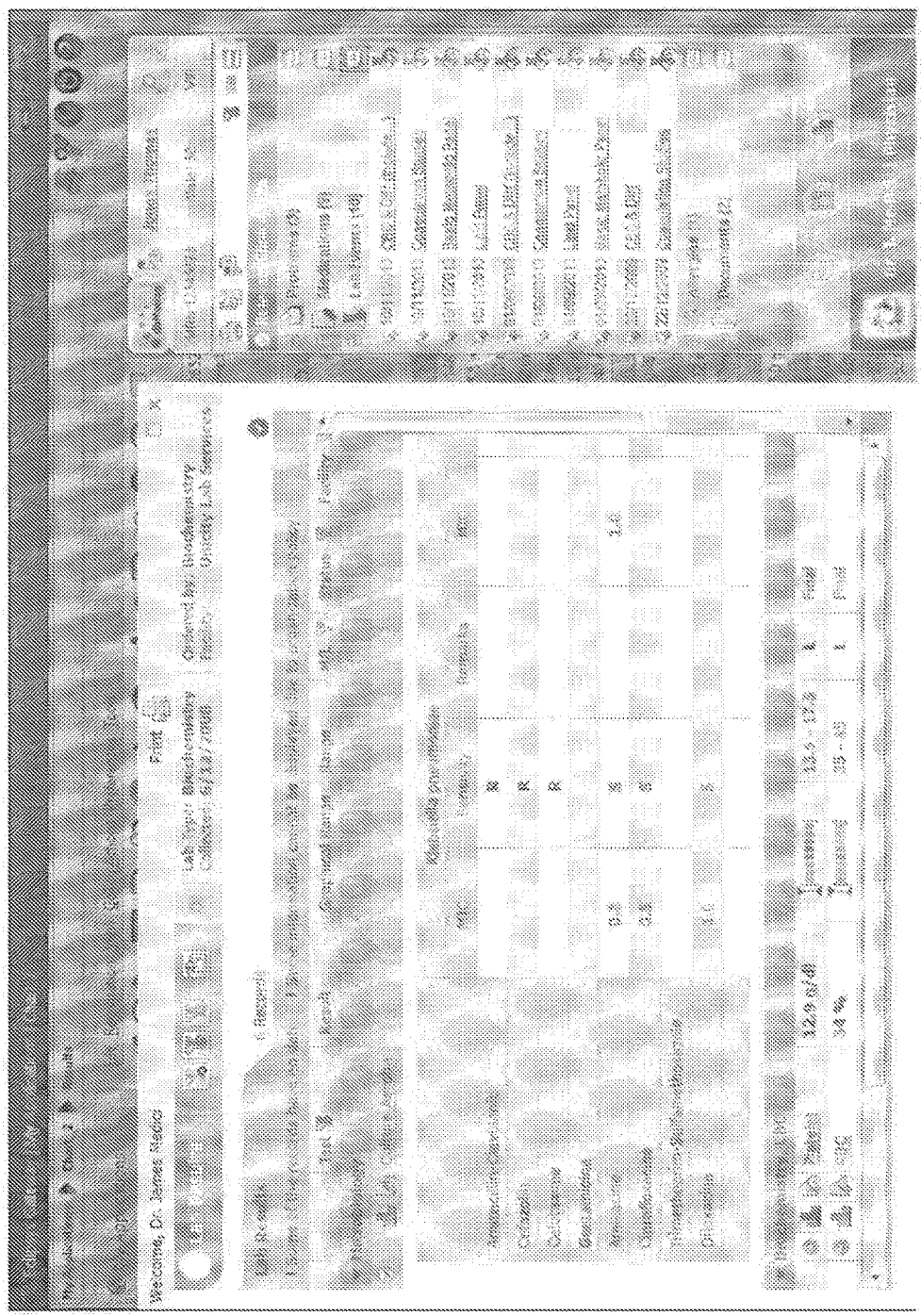
FIG. 5 is an example user interface for a laboratory screenshot of a preview panel useful in accordance with certain embodiments of the present invention.

FIG. 5 is a user interface for a laboratory screenshot of a preview panel useful in accordance with certain embodiments of the present invention.

Example Attention Rule Definitions for a Clinical Content Specification are now described. The smart agent typically uses attention rules to determine whether or not to provide a user with an indication that aims to direct her or his attention to the fact that information relevant to her or him is available in the HIES. The indication may include a highlight color in the background of the Name e.g. as shown in FIG. 6a. A rule can be built from a set of predefined filter types, such that a suitable predefined combination of the rules triggers the Attention indication and the relevant data presented by default. FIG. 6b is a table presenting an example set of basic rules. FIG. 6c is a table presenting an example set of rule combinations. The indication may consider the filter types of FIG. 6c which are combinations of the basic rules of FIG. 6b.

Example rules are as follows:

Rule 1: Exclude my EHR data:

User is alerted if there is information in the HIES which does not exist in the user's EMR. Typically, the HIES stores an indication, for each information item, of the EMR which provided that information item, allowing information items provided by a user's EMR to be filtered out and not displayed to the user.

Rule 2: Exclude data irrelevant to workflow.

A health care providing user opens his EMR at a page pertaining to laboratory, medicine, Procedures, Allergies, Vital signs, Pathologies, Imaging results, Clinical documents, immunizations, Problems, Diagnosis, or any other EMR functionality. The Agent hovers over the EMR application, intercepts the type of page opened, and selects from among the HIE information items available, only the ones which are relevant, using predetermined criteria, to the current EMR functionality.

Rule 3: new since last seen.

Smart agent generates an alert if information which is new, relative to the point in time at which a particular health care providing user last looked at the HIES.

FIG. 7a is a table of an example set of presentation use cases.

FIG. 7b is a table of an example set of context interception use cases.

FIG. 7c is a table of an example set of system health use cases.

FIG. 7d is a table of an example set of data preparation, configuration & deployment, and extension development use cases.

The high level architecture of a smart agent system constructed and operative in accordance with certain embodiments of the present invention is illustrated in the simplified functional block diagram of FIG. 1a. The apparatus of FIG. 1a may include some or all of:

1. VPO analyzer—an addition to the VPO Web Services. is typically operative to filter and highlight pieces in the VPO which are considered important to be presented. It is typically based on GetVPO functionality and rules on those.

2. SmartAgent application. A client-installed application.

Typically comprises some or all of:
  a. SmartAgentHost—a windows try application that connects all the dots on the client machine
  b. SmartAgentPresentation—SmartAgent presentation Module (WPF) application
  c. Context interception library—Library Screen capturing interfaces. Its job is to capture events from EMR application such as patient context, and pass it on to the SmartAgentHost.

Figure 8:
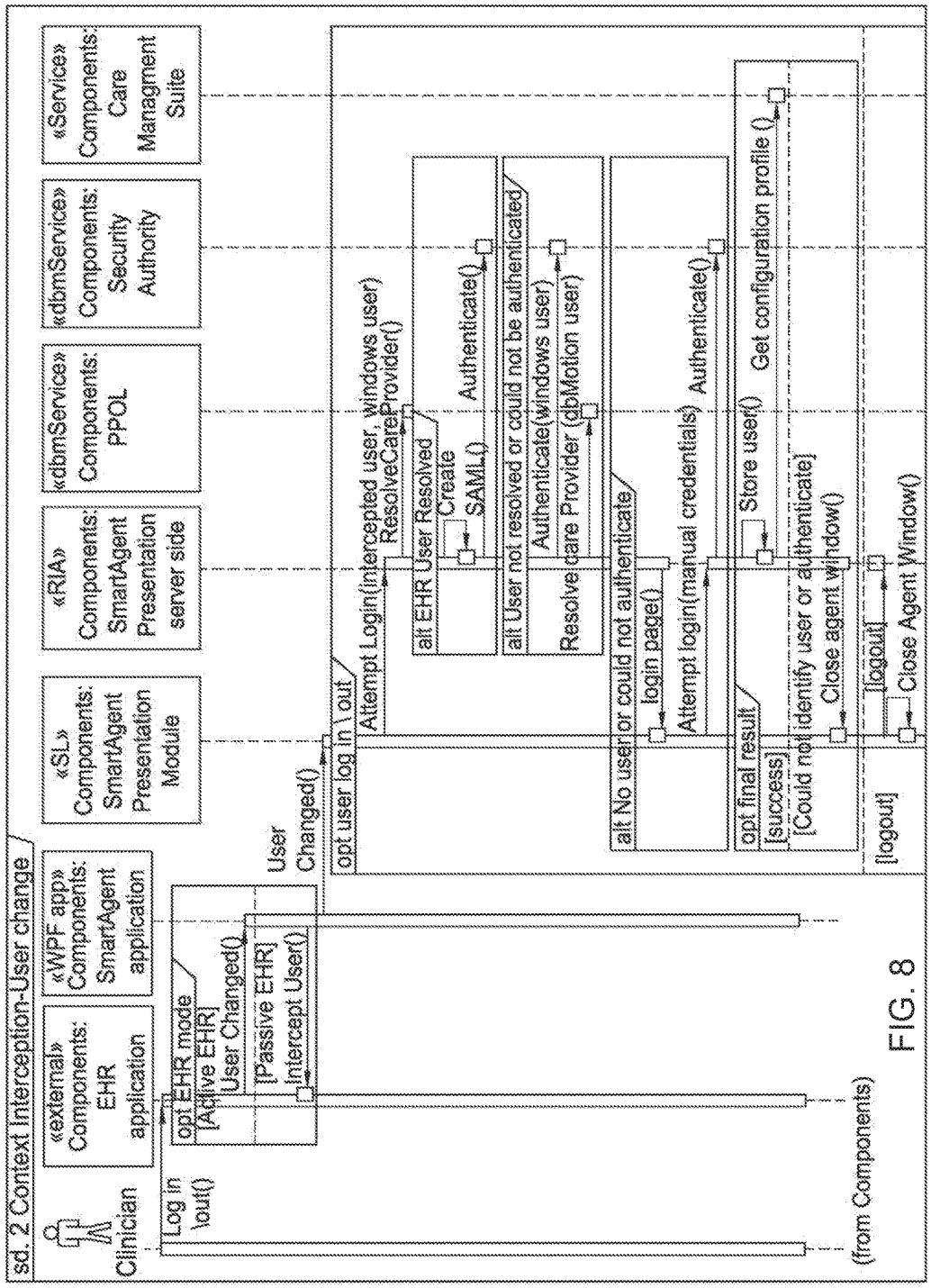
FIG. 8 illustrates an Interaction example—User context interception sequence, in Enterprise Architect UML format.

Certain user context interception sequences, some or all of which may be included in the model, are illustrated in the diagram of FIG. 8, which includes an Interaction example—User context interception sequence. FIG. 8 and other figures herein are generated in Enterprise Architect UML format; it is appreciated that this does not limit the scope of the invention and is merely utilized as one possible format for demonstrating one possible example set of data structures and computerized processing methods useful for implementing the present invention.

An example use case model is now described with reference to FIGS. 9, 10*a*-10*c*, 11-13.

Figure 9:
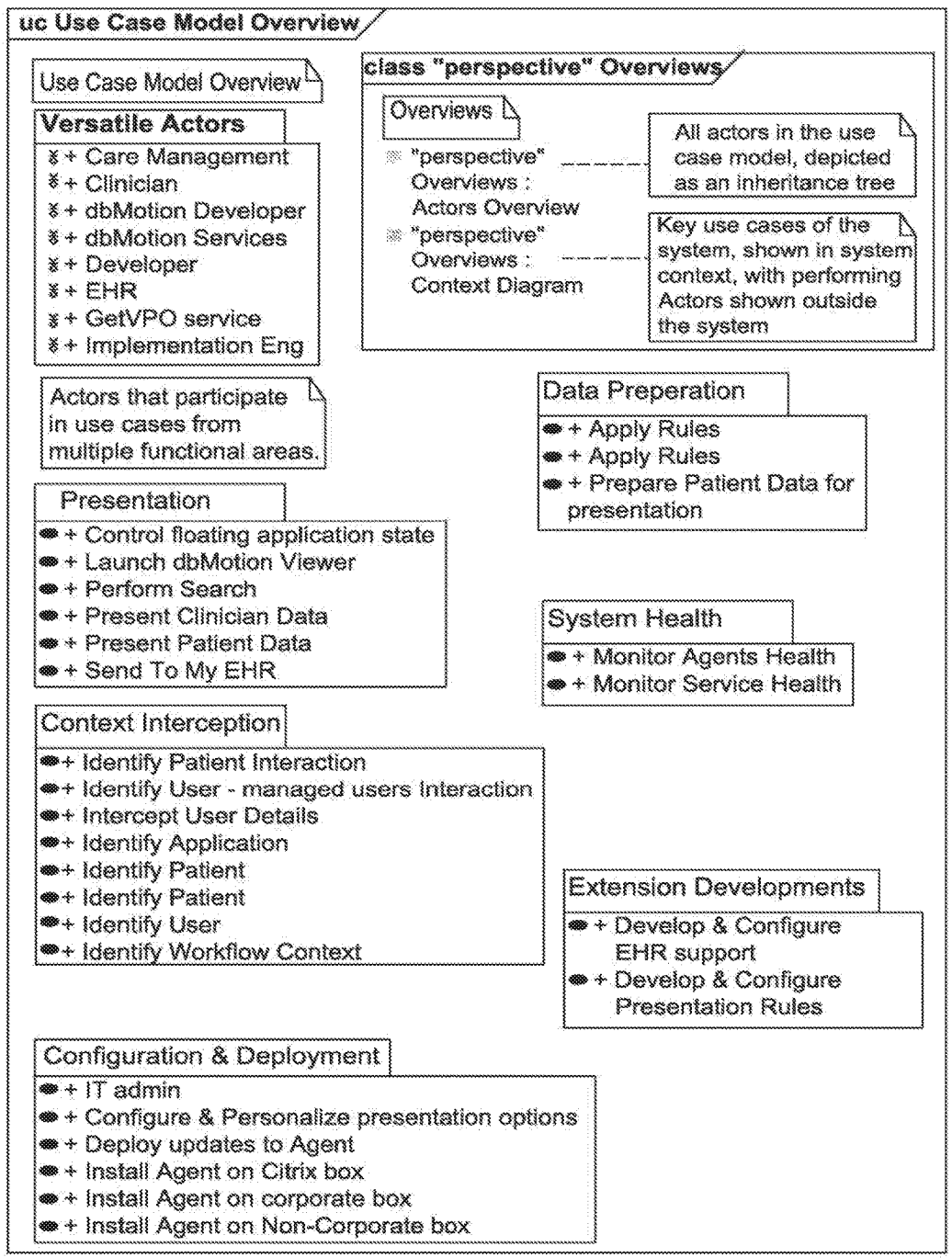
Figure 10A:
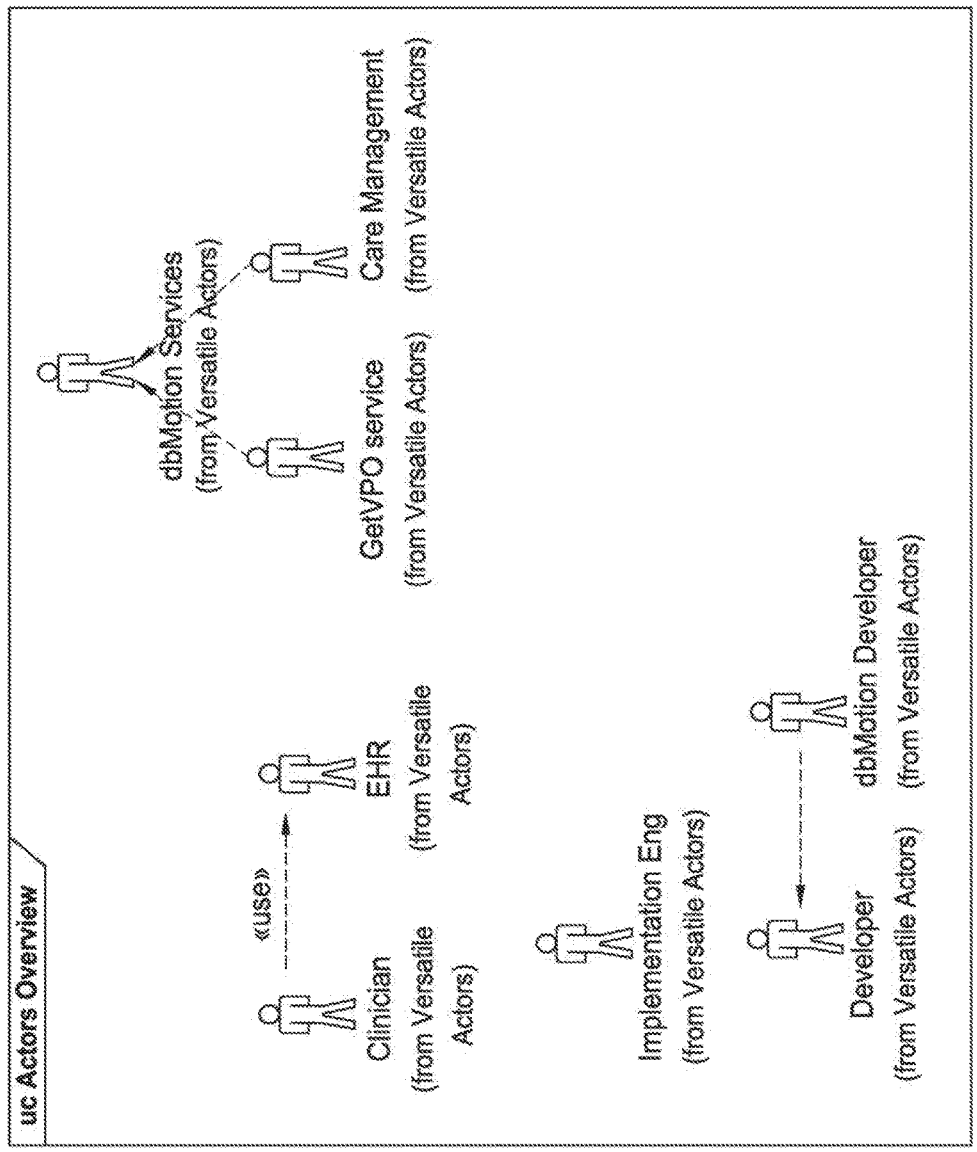
Figure 10B:
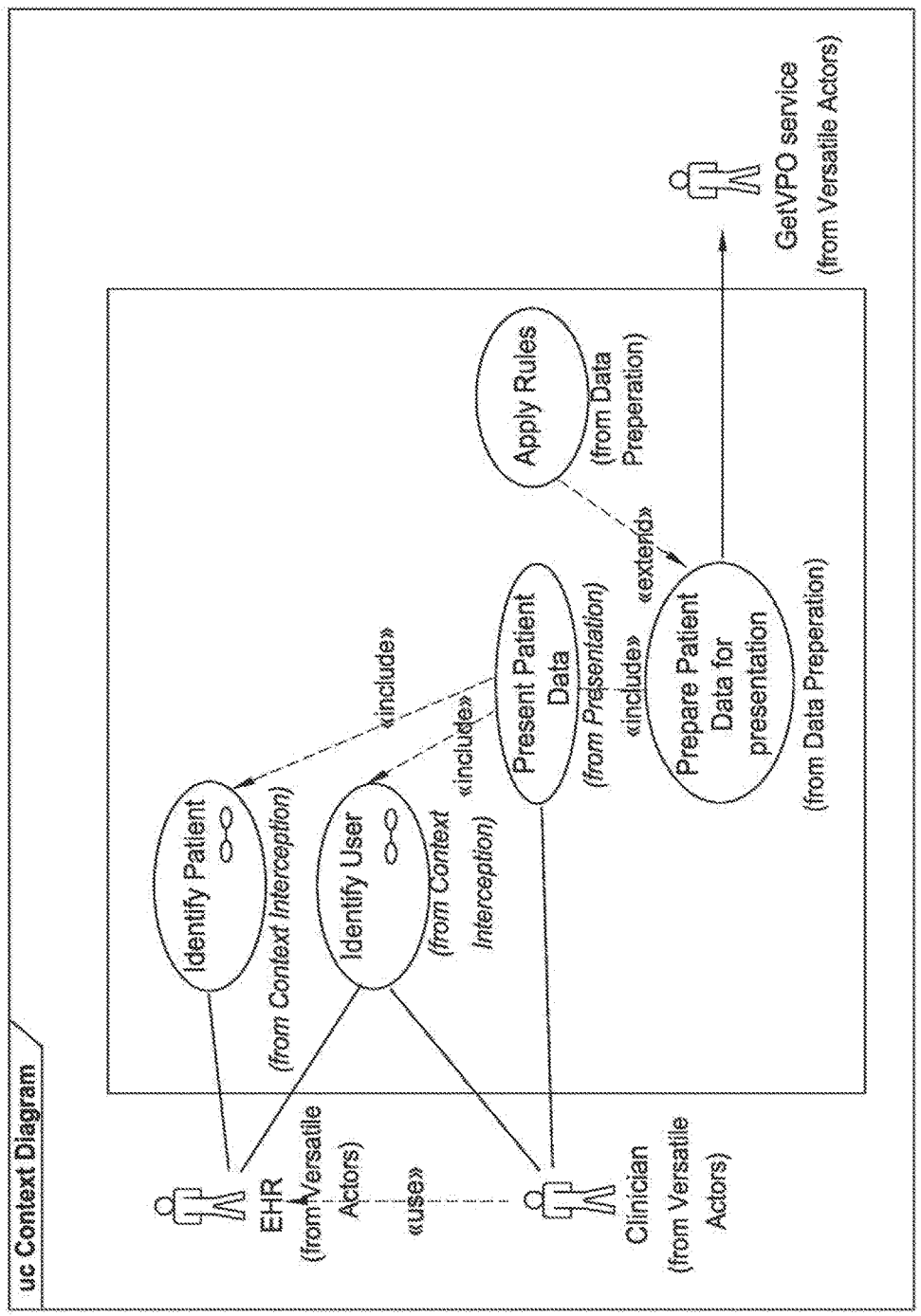

A Use Case Model Overview (Use Case diagram) is illustrated in FIG. 9. "Perspective" Overviews are illustrated in FIGS. 10*a* and 10*b* including an actors overview diagram and a use case context diagram, respectively.

Regarding the configuration and deployment functionality of FIG. 9:

Configure & Personalize presentation options may include, inter alia: Presentations Skins Vs EHR., Presentation rules and Base query, each of which is now described in detail according to respective embodiments of the present invention:

Presentation skins refers to an ability to customize the SmartAgent application appearance to have a plurality of different "look and feel"s. Typically, end users want the EMR agent to appear on top of a given EMR with a look and feel which is similar to that of the EMR.

Presentation Rules—refers to how the SmartAgent behaves to a given attention rule result—such as blinking frequency of alerts, or whether to blink and/or to expand the SmartAgent to view Clinical Data.

Base Query refers to filtering to obtain a VPO. Filtering can be by Time, or which clinical Aspects to obtain (e.g. filter to obtain only labs, or All Clinical Aspects).

For the "deploy updates to agent" use case, the system may update to the smart agent applications scattered all over the network (and out of network for community clinics). The smart agent may be installed on any suitable platform, such as a Citrix box. For the "install agent on Citrix box" use case, setting up the agent may be controlled by configuring Citrix sessions, or by network login script.

Figure 10C:
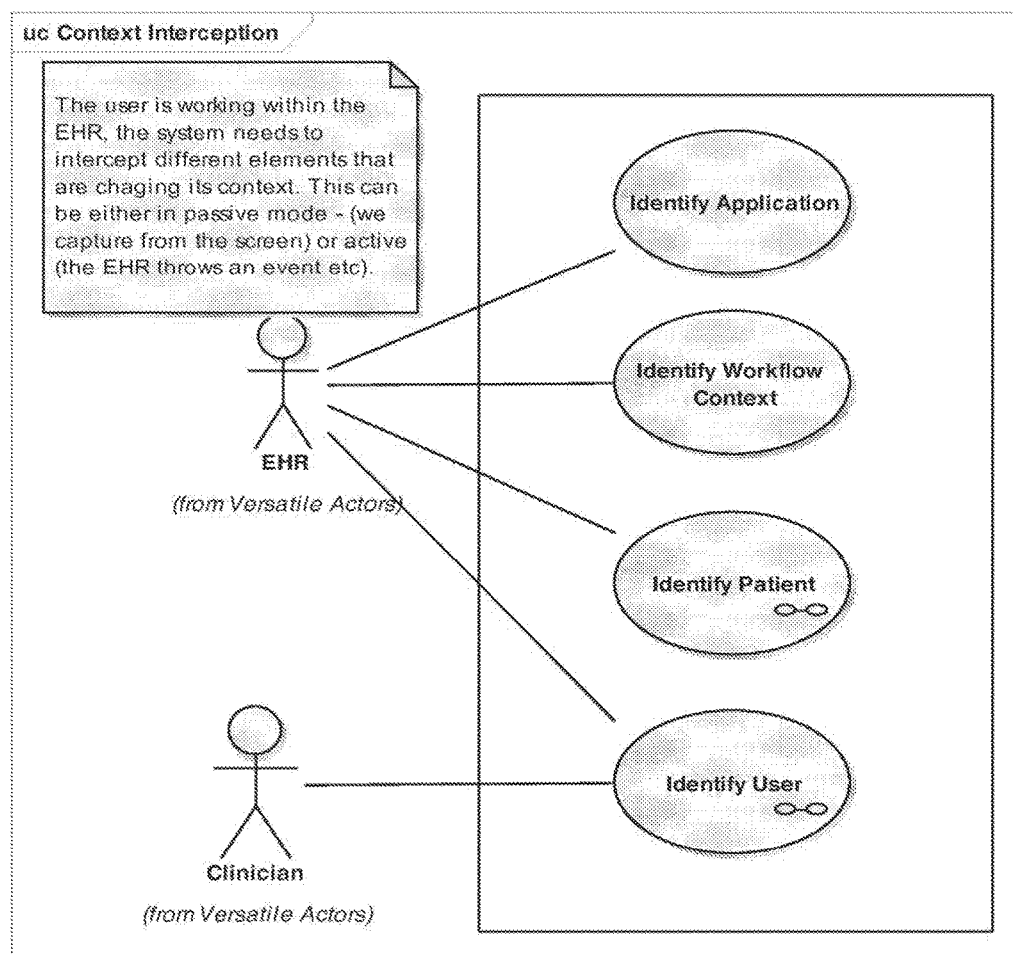

A Context Interception (Use Case diagram) is illustrated in FIG. 10*c*, which is suitable for implementing the context interception functionality of FIG. 9. Context interception may include identification, e.g. as described below, of some or all of: (a) application, (b) patient e.g. as per FIG. 11 described herein, (c) user, e.g. as per FIG. 14 described herein, (d) workflow context, (e) patient interaction, (0 user-managed user interactions, e.g. as per FIG. 14 described herein, and (g) user details e.g. as per FIG. 13 described herein. User identification may include interception of the users' details, and interception of user-managed user interactions.

Re "Identify Application" use case shown in FIG. 9: In this UC the system intercepts the application (EMR) which the user is using. For example, is the user working with Allscripts MyWay, Cerner etc. This context may be captured from the EMR screen or provided by the EMR. This same application can be used for multiple instances. For example a Cerner app may be used in different "regions" in UPMC—Cerner H1, H2, H3. The instance may be used when applying content rules such as "exclude mine".

Re "Identify Patient" use case shown in FIG. 9: In this UC the system intercepts the patient that the user is currently looking at in the EMR. This context may be captured from the EMR screen or provided by the EMR.

Re additional "Identify Patient" use case shown in FIG. 9: In this UC the system intercepts the patient that the user is currently looking at in the EMR. This context may be captured from the EMR screen or provided by the EMR.

Figure 11:
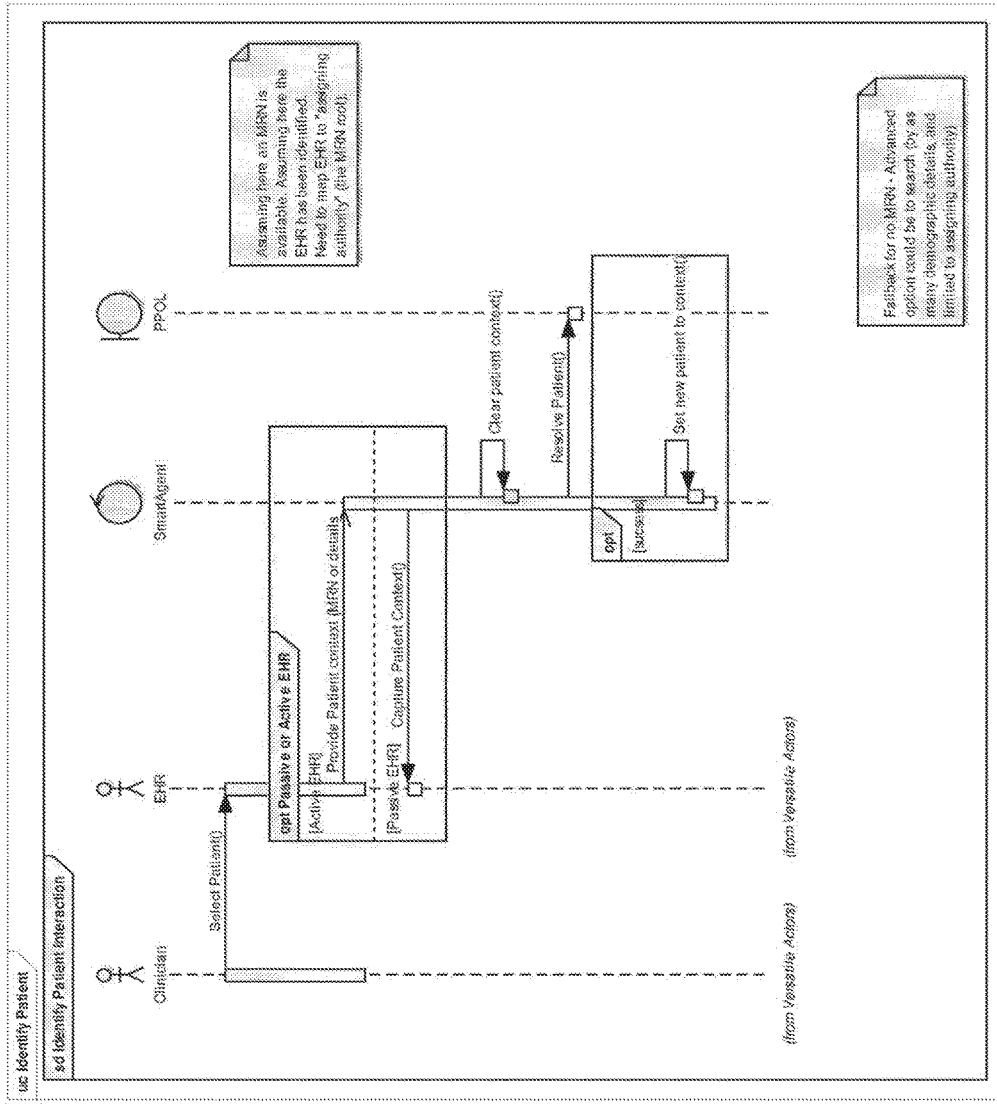

FIG. 11 is a Sequence diagram of an "Identify Patient" Interaction.

Re the "Identify User" use case shown in FIG. 9: In this UC the system intercepts the user that is using the EMR in order for the health information exchange system (HIES) to present data to that user, according security privileges as configured in the EMR. This context may be captured from the EMR screen or provided by the EMR.

Figure 13:
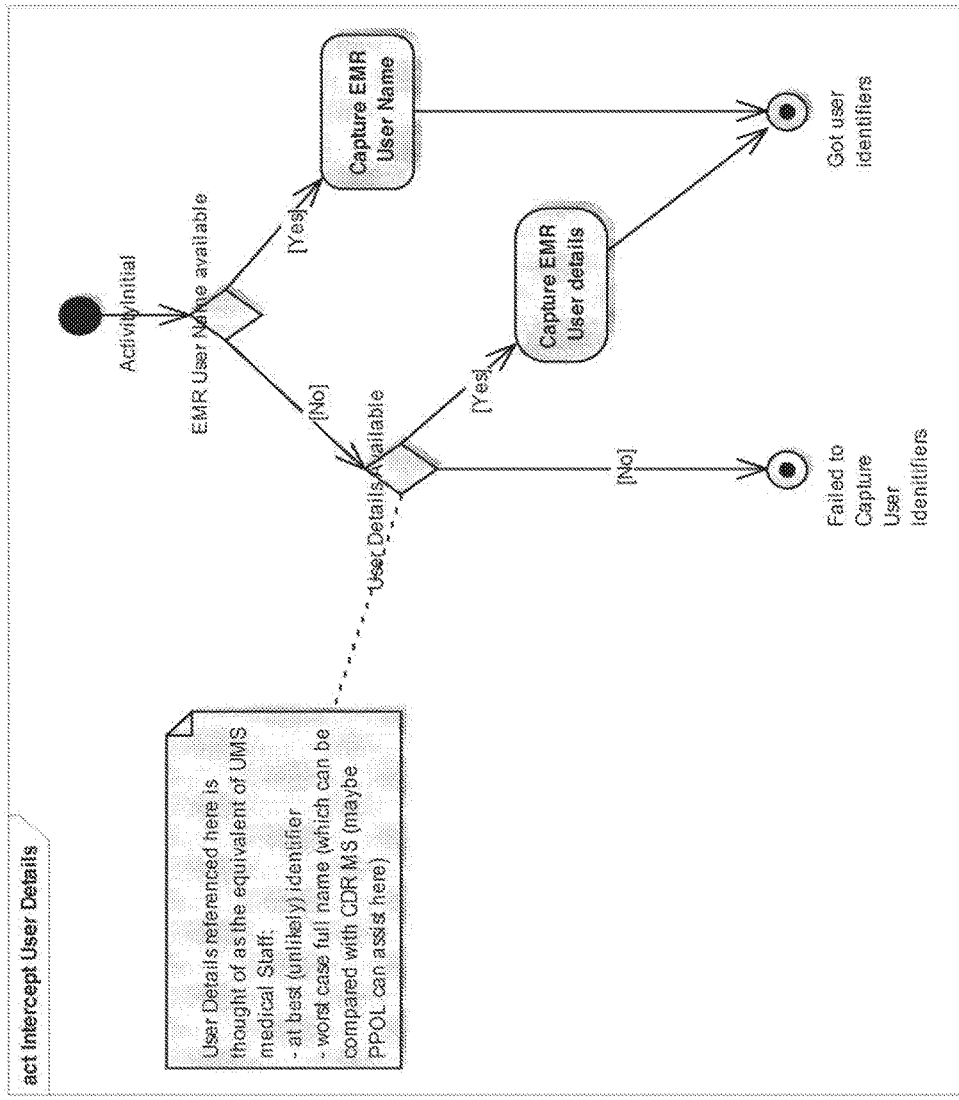

FIG. 13 is an Activity diagram of an "Intercept User Details" functionality.

Figure 14:
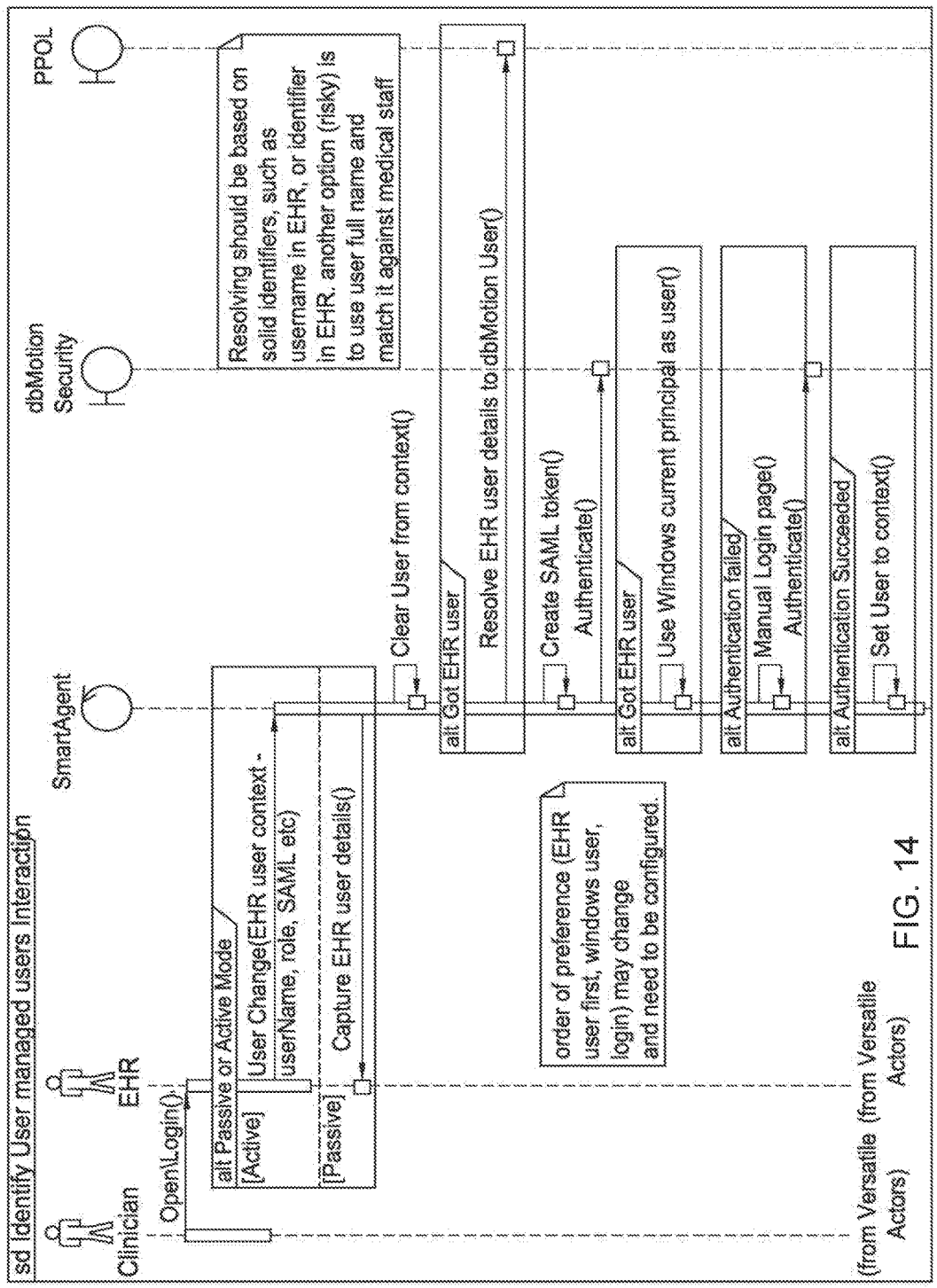
FIG. 14 is a Use Case diagram of an "Identify User" functionality which is useful e.g. in conjunction with the "Identify User—managed users Interaction" use case shown in FIG. 9.

FIG. 14 is a Use Case diagram of an "Identify User" functionality which is useful e.g. in conjunction with the "Identify User—managed users Interaction"" use case shown in FIG. 9.

Re the "Identify Workflow Context" use case shown in FIG. 9: In this UC the system intercepts the workflow in which the user is on the EMR side. For example, is the user on "labs" tab or on "medication" tab? This context may be captured from the EMR screen or provided by the EMR. An advanced scenario here is responding to "free" selection on the screen, e.g.—user selects "Hgb" on the screen and history graph needs to be shown.

Turning now to the Data Preparation functionality in FIG. 9:

Re the "Apply Rules" use case: Typically, acting on patient data, the system decides which records are to be presented using attention rules e.g. as described herein. The system is typically able to add more rules and adjust existing rules. Example rules include:—"exclude my EMR data" and—"exclude what I saw", also termed herein the "new since last seen" rule.

Re the "Prepare Patient Data for presentation" use case: typically, the system prepares data to be presented to the user. This includes fetching the data as well as filtering out irrelevant records, based on rules. This typically works in conjunction with the VPO analyzer of FIG. 1*a*.

Re the Extension Developments functionality in FIG. 9:

The "Develop & Configure EMR support" UC typically describes a possible need of the system to grow and support new EMRs, new versions of known EMRs as well as customized versions of known EMRs. The support is focused on the interception of elements from the EMR screen.

Re the Presentation functionality in FIG. 9:

The "Control floating application state" may for example include Minimize, expand, size, position, dock, close etc. In the launch health information exchange system (HIES) Viewer UC the system acts merely as an entry point to the existing viewer (Clinical Viewer, Collaborate). The launch may or may not include context (user, patient, app). For example—navigation menu for medications (even though no medication record is currently shown). In the "Perform Search" UC the user searches for records within the patient record. The search can either be on the codified data, or free search over text (notes within acts and the content of clinical documents). In the "Present Clinician Data" UC the system presents data from the HIES that is not related to the patient viewed in the EMR. For example—"my recent events" from a Collaborate functionality in the HIES, "my admitted patients" and so on.

In the Present Patient Data UC the system presents patient data to the user. In the "Send To My EMR" UC the user selects act to be sent to his EMR and the system delivers them to the EMR to be presented there.

The GetVPO service of FIG. 9 is an Actor which represents clinical services or Web Services which provides the ability to query and retrieve Patient clinical Data.

Figure 15:
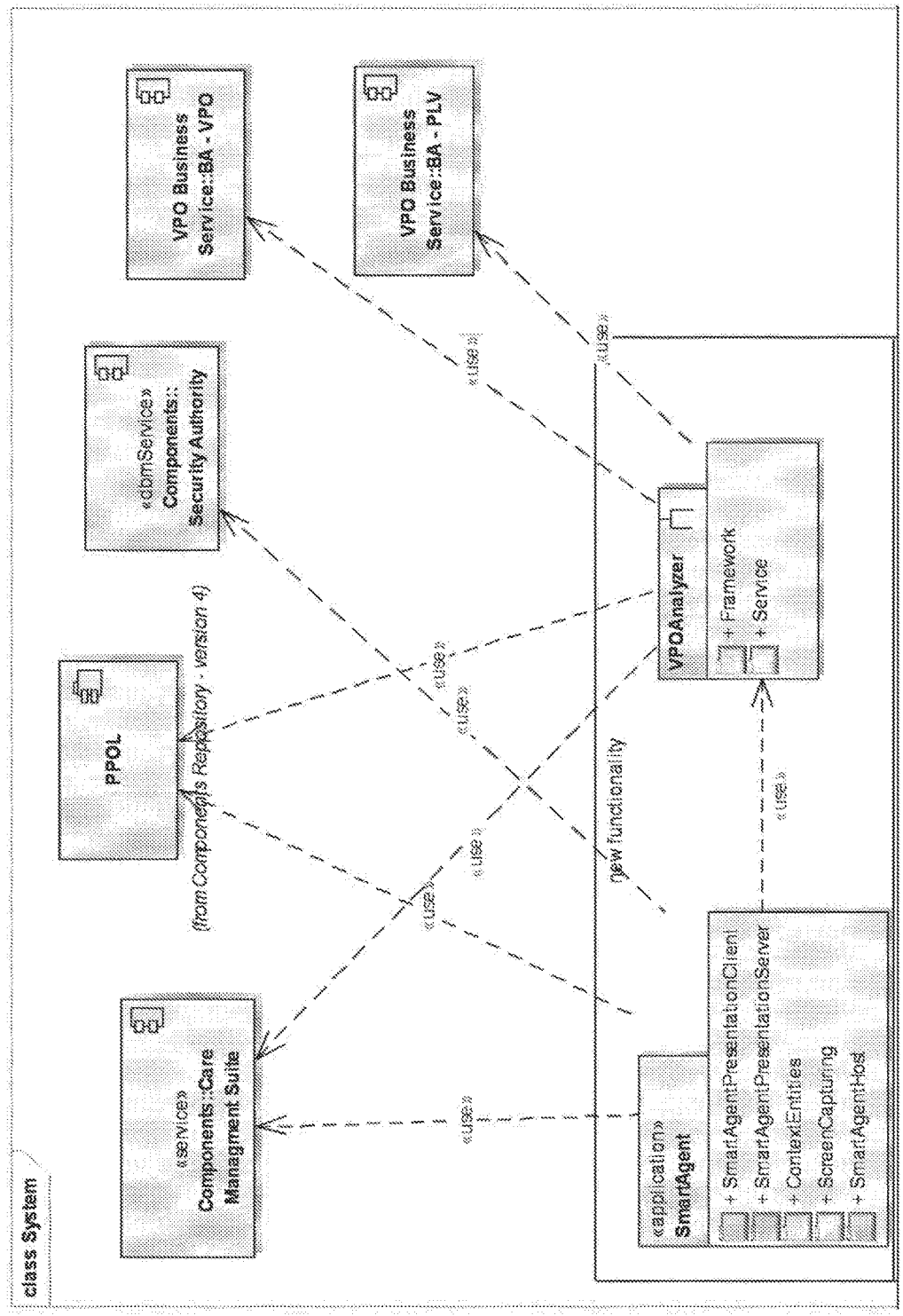
FIG. 15 is a diagram of an example Design Model of a smart agent constructed and operative in accordance with certain embodiments of the present invention.
Figure 16:
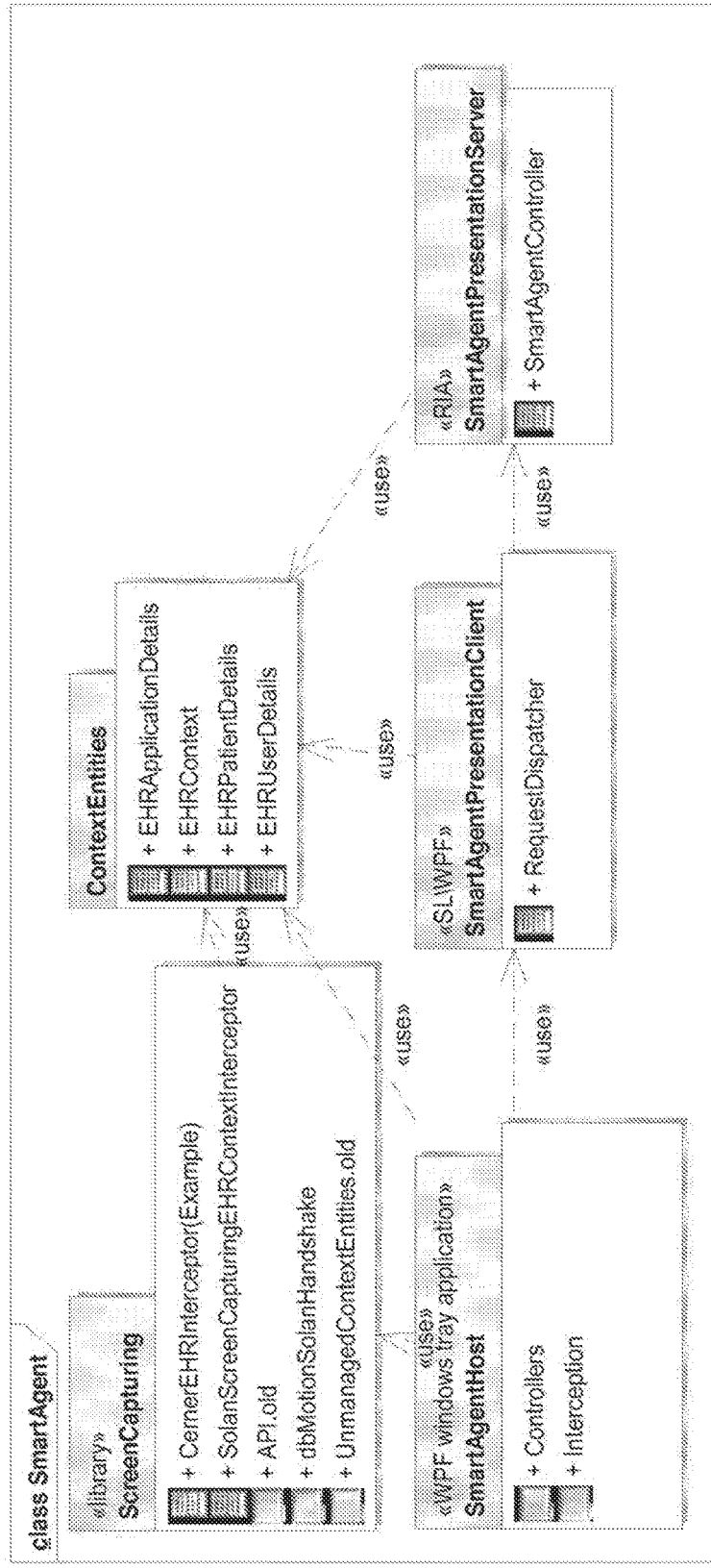
FIG. 16 is a logical diagram of the smart agent of FIG. 15 according to certain embodiments.

An example Design Model is shown in FIG. 15. FIG. 16 is a logical diagram of the smart agent of FIG. 15.

Figure 17:
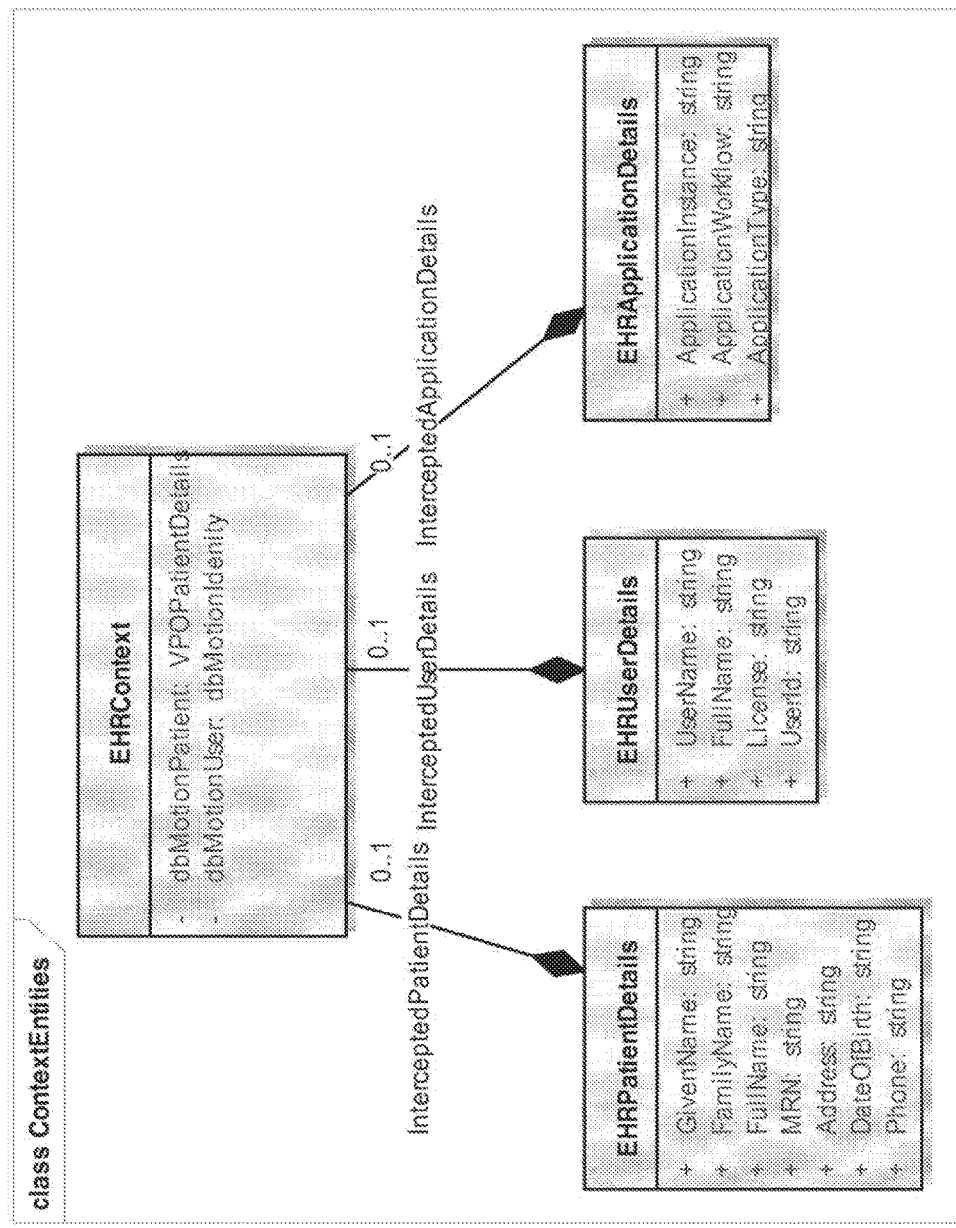
FIG. 17 is a logical diagram of the context entities of FIG. 16 according to certain embodiments.

FIG. 17 is a logical diagram of the context entities of FIG. 16. The context entities package may serve as the data contract of the event model between all components. EHRContext may comprise an entity (data) object representing the context of a specific EMR application. EHRApplicationDetails may represent the application (EMR) details as intercepted. EHRPatientDetails may represent the patient details as in the EMR intercepted. EHRUserDetails represents the user details in the EMR as intercepted.

Figure 18:
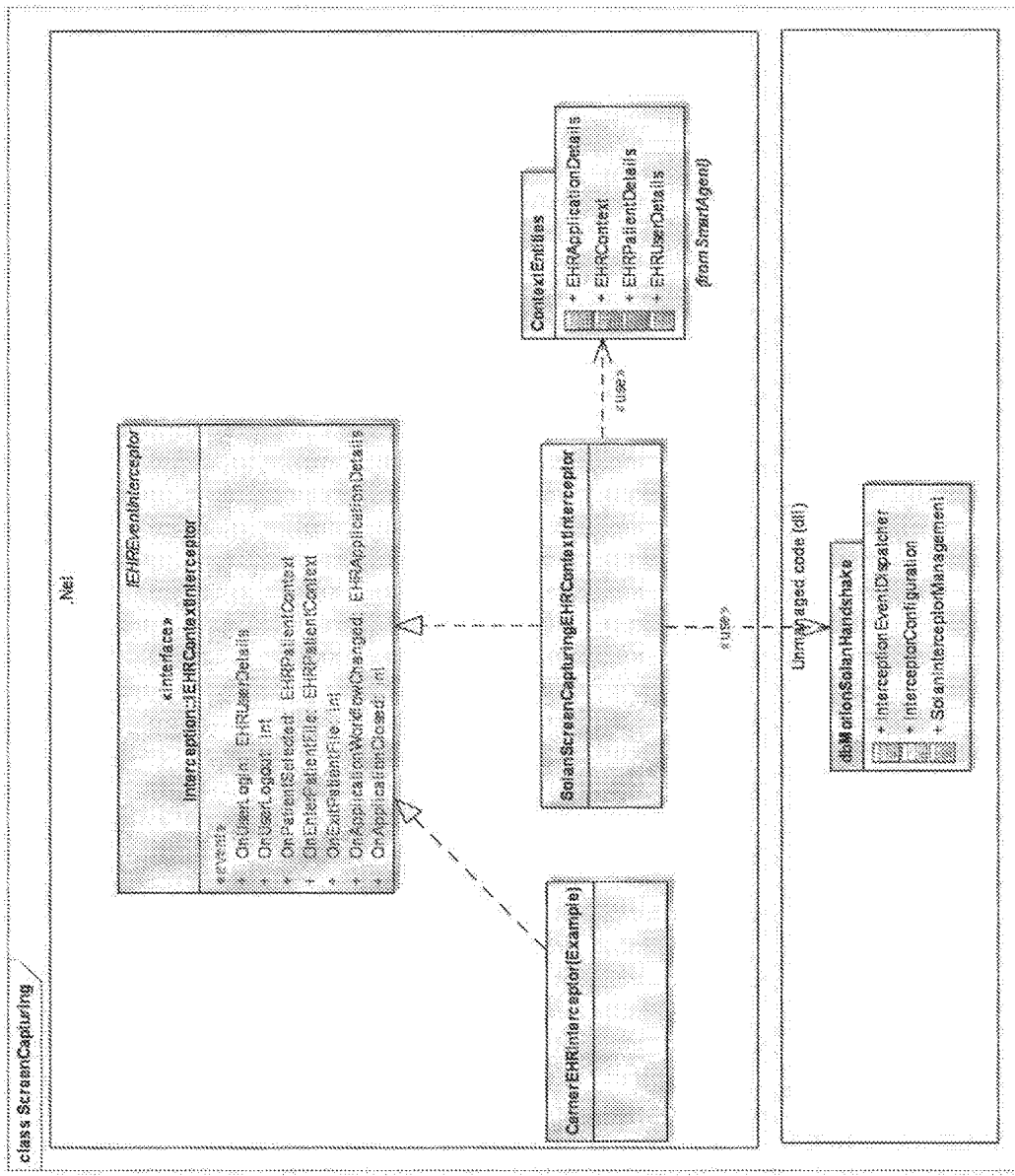
FIG. 18 is a logical diagram of the ScreenCapturing functionality of FIG. 16 according to certain embodiments.

The screen capturing functionality of FIG. 16 typically comprises a library that implements in an IOC (Inversion Of Control) implementation of the Screen capturing interfaces. Its job includes capture of events from an EMR application such as patient context, and passing the patient content on to the AgentHost of FIG. 16. FIG. 18 is a logical diagram of the ScreenCapturing functionality of FIG. 16.

The ScreenCapturingEHRContextInterceptor of FIG. 18 may comprise an interceptor based on conventional Screen Capturing technology which may operate the dlls and convert to .Net events as appropriate.

The ScreenCapturingEHRContextInterceptor of FIG. 18 may comprise any interceptor based on suitable Screen Capturing technology such as that commercially available from screenscraper studio, having a http presence on the world wide web at at: screen-scraper.deskperience.com// which is a software tool including a development kit that is capable of screen capturing actions.

The SmartAgentHost functionality of FIG. 19 typically is installed on the client machine, hosts the presentation layer and orchestrates the interaction between the presentation layer and the screen interception e.g. screen capturing.

Figure 21:
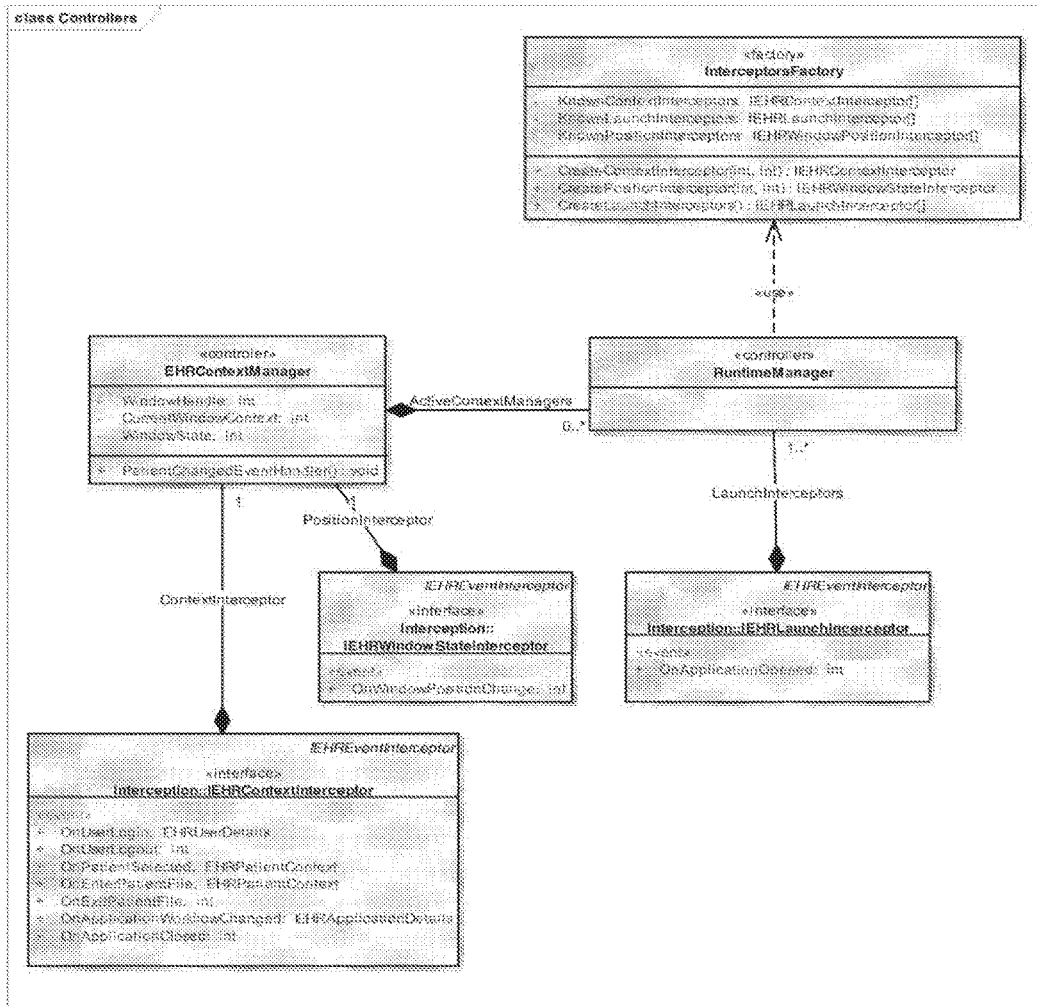
FIG. 21 is a Logical diagram of controllers according to certain embodiments.

A logical diagram of controllers is shown in FIG. 21. FIG. 21 illustrates the engine and the corresponding configurations that execute and orchestrate the various interceptors shown and described herein. Typically, the apparatus of FIG. 21 is useful in conjunction with the screen capturing functionality of FIGS. 16 and 18. FIG. 21 is particularly useful in understanding an example design of context interception, its classes and methods, and scenarios the context interceptor may support, such as but not limited to one or more of: user log-in, enter patient file, exit patient file, all according to certain embodiments of the invention. The diagram of FIG. 20 describes, for the above scenarios, an initial step of getting the context and passing it to an EMR agent, so as to call VPO services, search patient and security, all in accordance with certain embodiments of the invention.

Regarding the EHRContextManager of FIG. 21, it is typically the responsibility of this class to orchestrate the context switches, bridging between context interceptors, presentation parts, and windows events, such as but not limited to:

a. Pass on events to the presentation about patient, user, application and workflow context switches
b. Receive events from presentation such as user requests to hide\ close\float the window and make sure to respond correctly to those events, for example by stopping the interceptors.
c. Make sure the window moves together with the EMR window.

The multiplicity of this class may be expected to be one per EMR window instance. (e.g. two Cerner windows would be assigned with two different context managers.

Operations, some or all of which may be performed by the InterceptorsFactory functionality of FIG. 21, are set out in the table of FIG. 22.

The RuntimeManager of FIG. 21 typically hosts the entire system. Its responsibilities include some or all of the following:
1. Manage (start\stop\monitor) the different managers.
2. Orchestrate the process of discovering new EMR window, creating a ContextManager and context interceptor for it.

Figure 23:
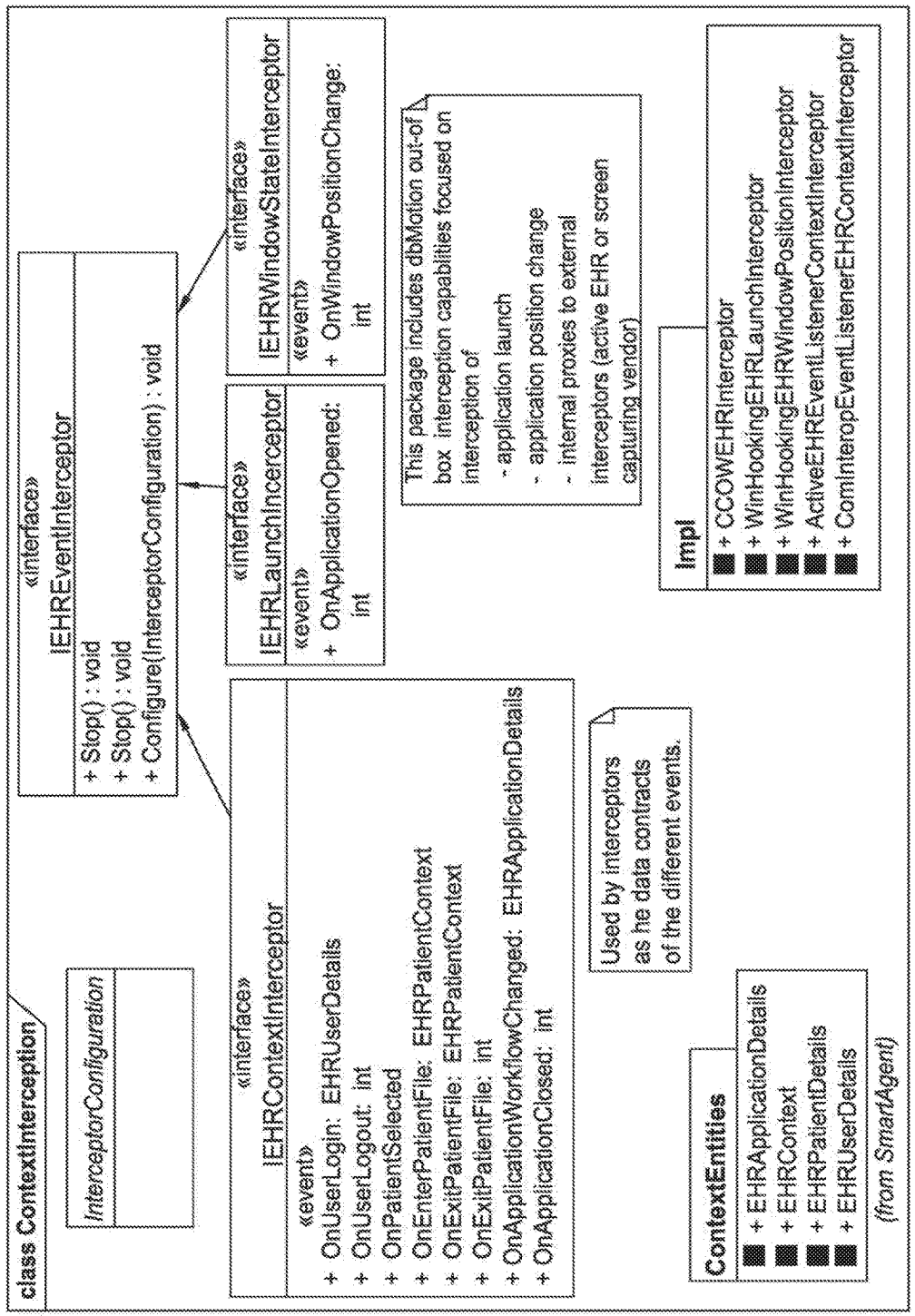
FIG. 23 is a logical diagram of Context Interception functionality provided according to certain embodiments.
Figure 31:
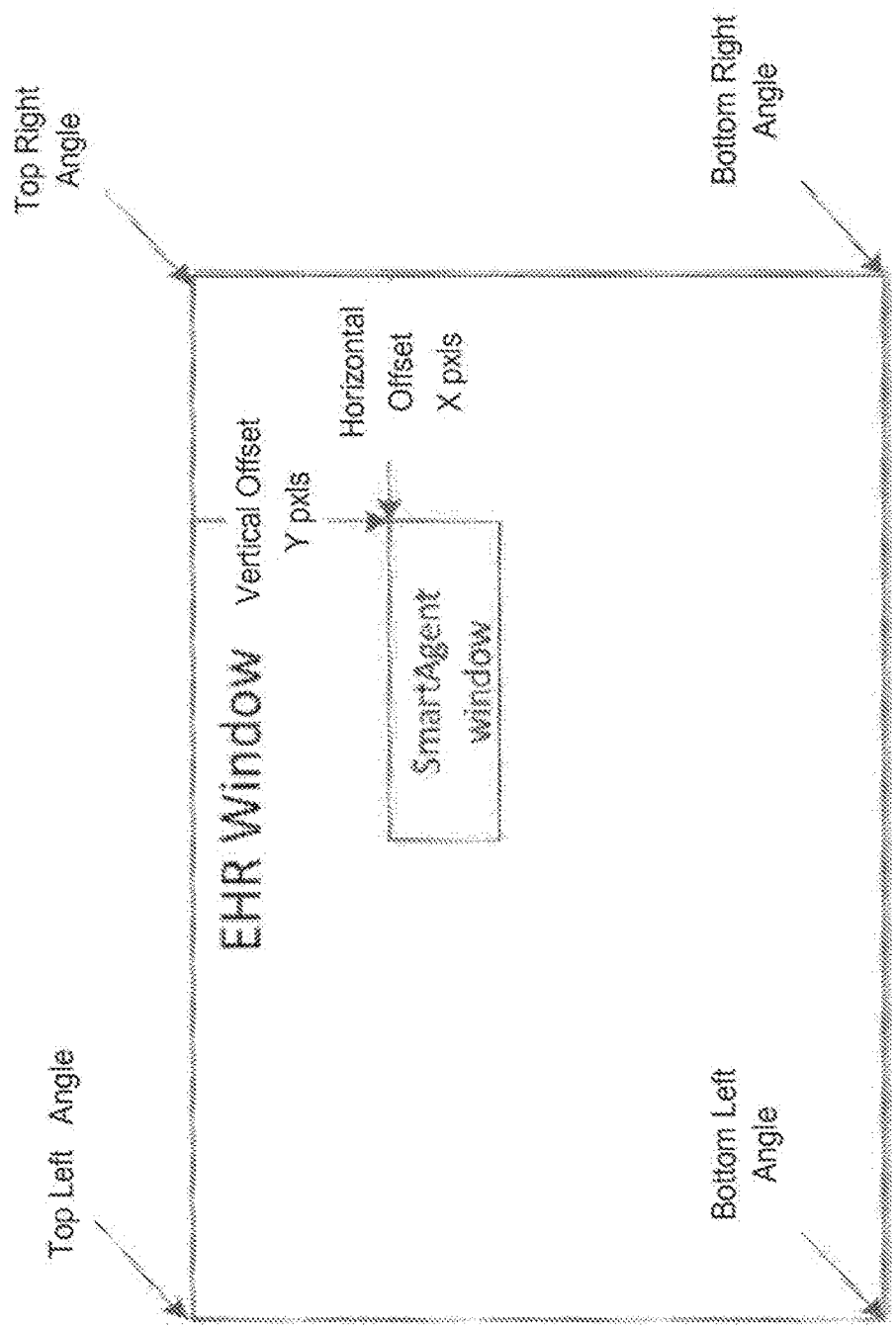
FIG. 31 is a pictorial diagram showing parameters useful for defining EMR Agent shell window position relative to EMR application window according to certain embodiments.

A logical diagram of ContextInterception is illustrated in FIG. 23. The InterceptorConfiguration of FIG. 25 typically comprises an object which may be delivered to each interceptor when it is started. The configuration is stored and controlled. The InterceptorConfiguration may hold a configuration of the Interceptor in the context of the EMR it intercepts. An example configuration is as follows:

a. Connection to Server
To allow an EMR Agent work with a database such as a dbMotion database an address of the server, e.g. dbMotion server, is typically set up. The Server address is typically a URL which may for example have an http: prefix followed by, say:
//ApplicationServer:9150/dbMotion/SmartAgent b. View shell window position:
  EMR Agent shell window position may be defined relatively to EMR application window. The View can be anchored to one of the sides of EMR window. Suitable parameters may specify relative position such as some or all of the following parameters as defined in FIG. 31:
    EMR angle—angle of EMR window to be used as a start point for computing View position
    View angle (Shell angle)—angle of View to be positioned relatively to EMR angle
    Horizontal offset—horizontal offset of View angle from EMR angle (can be negative to position View angle to the left from EMR angle)
    Vertical offset—vertical offset of View angle from EMR angle (can be negative to position View angle above EMR angle)
    Each time EMR window position or size is changed, EMR Agent typically updates corresponding shell window position e.g. according to the parameters above.
  View position parameters may be specified in a InterceptionConfig.xml file under a ShellConfig tag. Here is an example of suitable ShellConfig values:
    <ShellConfig
      EhrAngle="RightTop" ShellAngle="RightTop"
      HorizontalOffset="10" VerticalOffset="10" />
  These parameters may be specified per EMR.

c. SmartAgent Floating Application Attention rules may be as follows:
  The EMR Agent view title area may be used to notify the user when context dependent data is delivered to the Agent from a suitable database e.g. dbMotion database. The notification may have some or all of the following 3 parameters:

Blinking number—how many time title area blinks after some data is delivered

Blinking rise time—duration of each blink

Blinking pause time—delay between blinks

These parameters can be changed in a suitable file e.g. "dbMotion.SmartAgent.Client.Viewer.dll.config".

There follows an example fragment of the configuration file with default values:

```
<setting                name="BlinkingNumber"
    serializeAs="String">
    <value>5x</value>
</setting>
<setting                name="BlinkingRiseTime"
    serializeAs="String">
    <value>00:00:00.2000000</value>
</setting>
<setting                name="BlinkingPauseTime"
    serializeAs="String">
    <value>00:00:00</value>
</setting>
```

These parameters may be specified globally.

Figure 25:
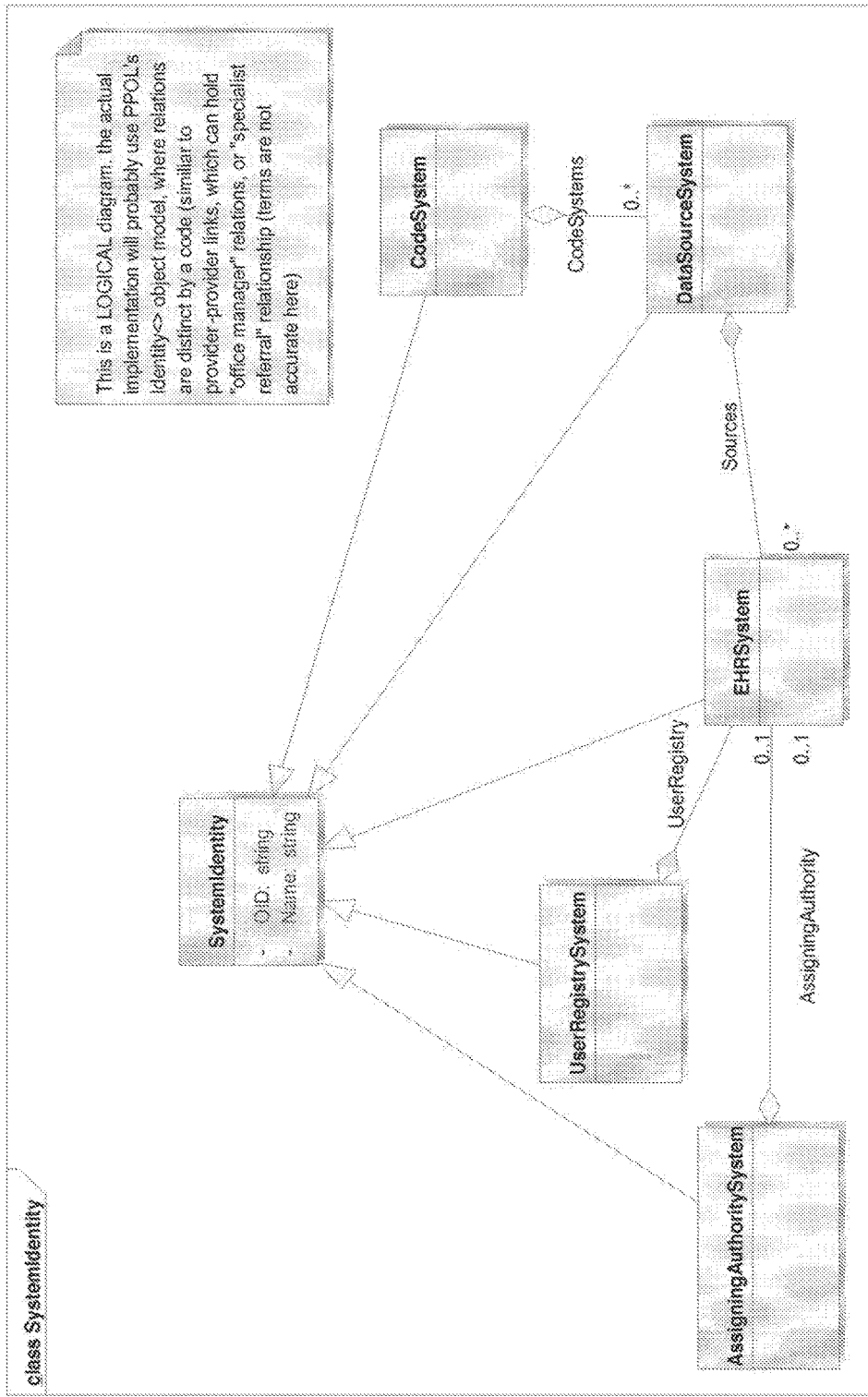
FIG. 25 is an example Logical diagram for the SystemIdentity functionality of FIG. 24.

The IEHRContextInterceptor of FIG. 25 is an interface; the responsibility of implementer of this interface typically includes discovery of context changes to a given EMR window instance. The window's assigned context manager may be subscribed to the interceptor's events.

The IEHREventInterceptor of FIG. 25 typically comprises an "abstract" interface which only defines the minimal requirements.

The IMpl package of FIG. 25 includes out-of-box interception capabilities focused on interception of some or all of: application launch, application position change, internal proxies to external interceptors, including, e.g. active EMR or screen capturing vendor.

Regarding the IEHRLaunchIncerceptor functionality of FIG. 25, the responsibility of the implementer of this interface is to intercept the event of launching a known EMR application. Once launched, a dedicated EHRContextInterceptor may be created to the specific window.

The runtime manager may be subscribed to the OnApplicationOpened event.

The IEHRWindowStateInterceptor of FIG. 25 typically comprises an interface operative to allow the application to stick into the EMR window and track it as it moves.

Referring again to FIG. 15, the VPOAnalyzer is an addition to the VPO "family" e.g. clinical data services as described herein and is operative to filter and highlight important pieces in the VPO to be presented. It is based on GetVPO functionality and rules pertaining to that functionality, typically including some or all attention rules applicable to the patient clinical data retrieved as described herein in detail.

Figure 24:
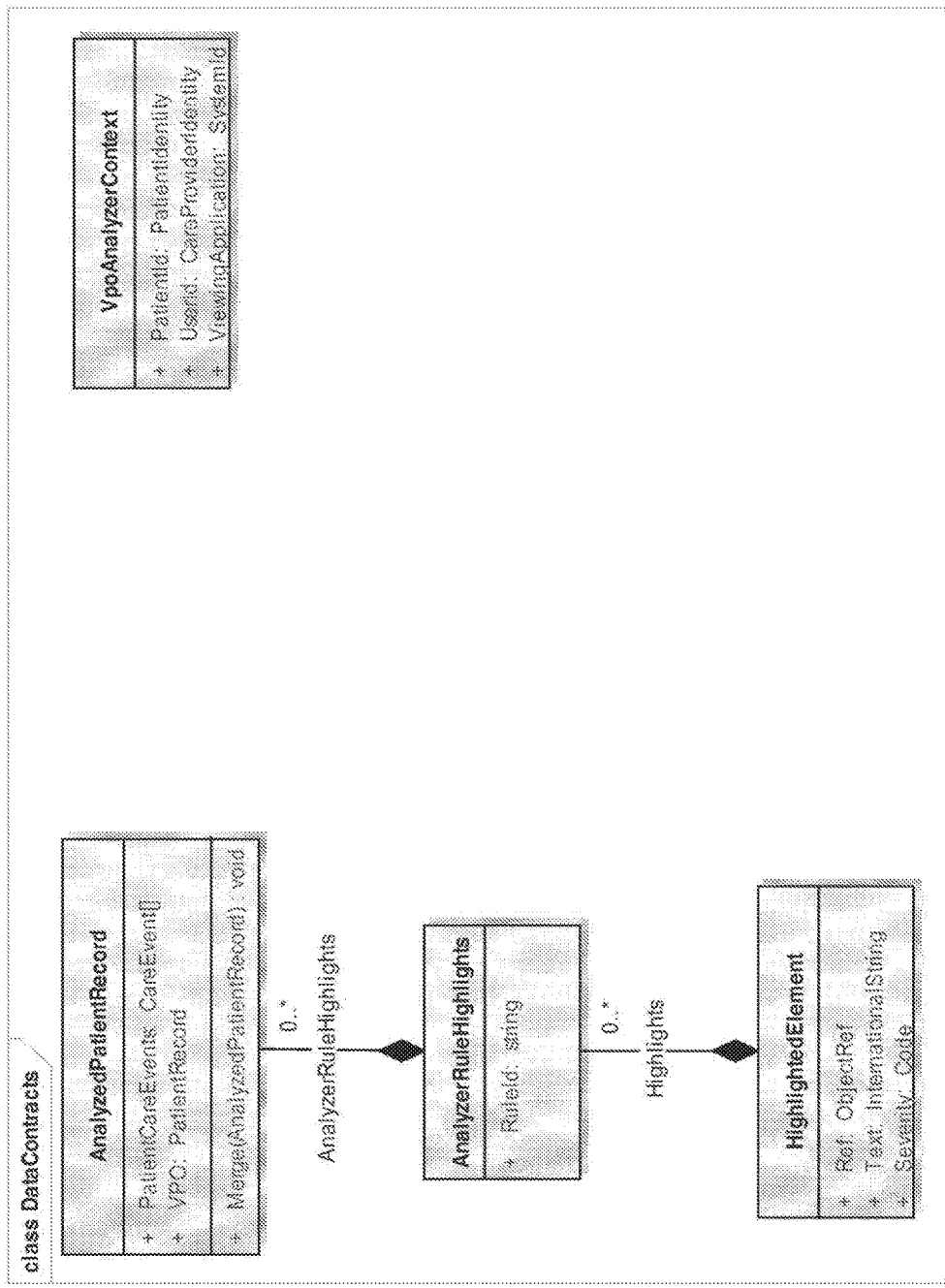

Example Framework and Contracts pertaining to the VPOAnalyzer may be appreciated with reference to FIG. 24. The AnalyzedPatientRecord of FIG. 24 typically provides a Data Contract for the VPO analyzer of FIG. 1a, containing the VPO as well as the markup—the highlighted elements of the VPO. The AnalyzerRuleHighlights of FIG. 24 typically holds the VPO markup highlights for an analyzer rule. The HighlightedElement of FIG. 24 typically allows the rule to mark \ highlight VPO elements to be presented according to their logic, for example—those that do not come from a given EMR. The SystemIdentity of FIG. 24 typically comprises a data contract package which may optionally be part of PPOL of FIG. 15.

FIG. 25 is an example Logical diagram for the SystemIdentity functionality of FIG. 24.

Figure 26:
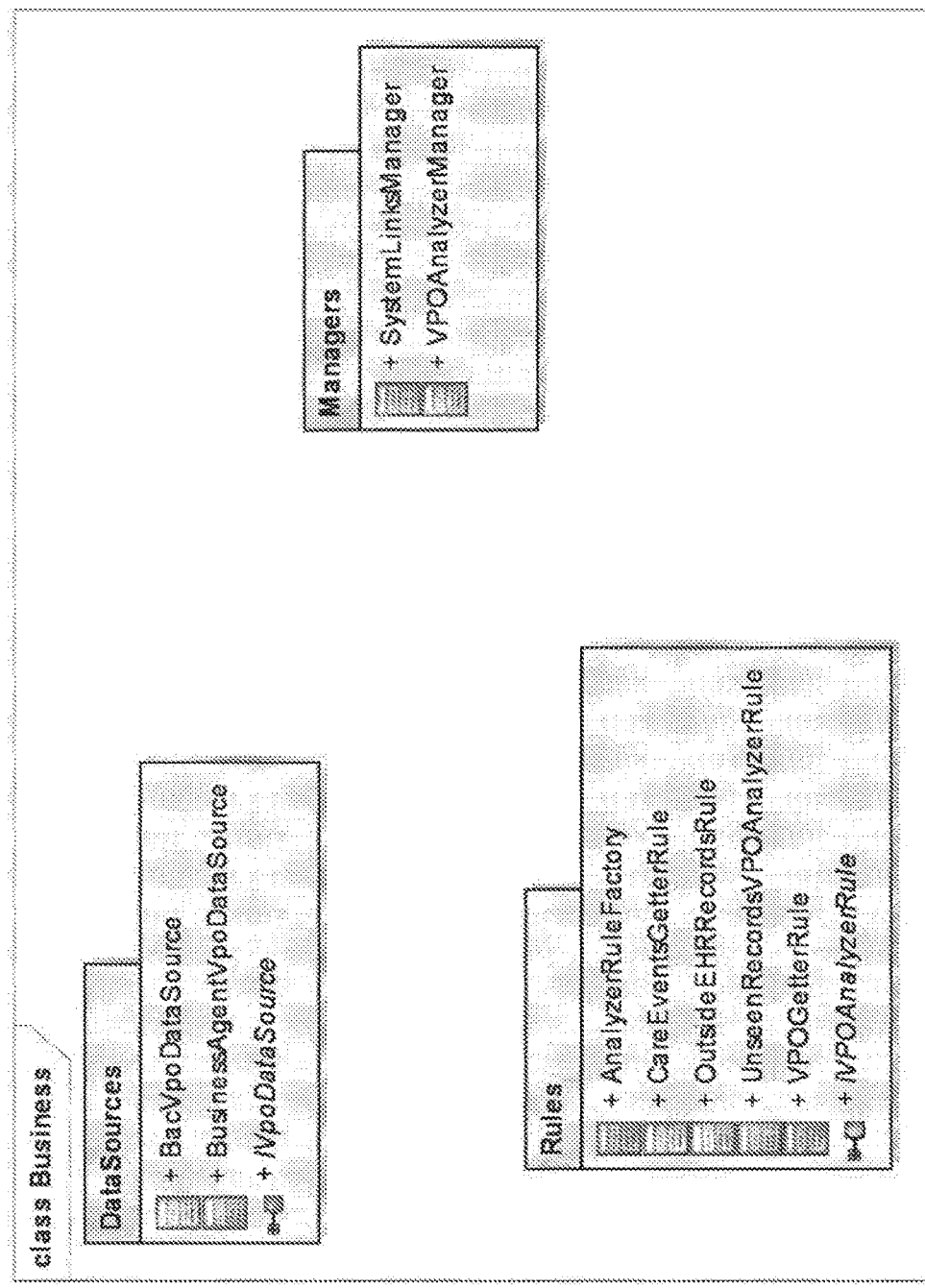
FIG. 26 is a logical diagram of Service & business layers provided according to certain embodiments.

Service & business layers may include the apparatus shown in the logical diagram of FIG. 26. The IVpoDataSource of FIG. 26 may comprise an interface which abstracts away the details of how the VPO is retrieved. A BAC-based data source for deployment outside "business" areas is provided and a business-agent version may be used when integrated into business access services hence it can utilize internal features. The SystemLinksManager of FIG. 26 may be part of the PPOL of FIG. 15 and typically comprises a manager responsible of providing configuration of system links and the relation between them. The VPOAnalyzerManager of FIG. 23 may comprise a manager\controller responsible of orchestrating the VPO analysis process.

Figure 27:
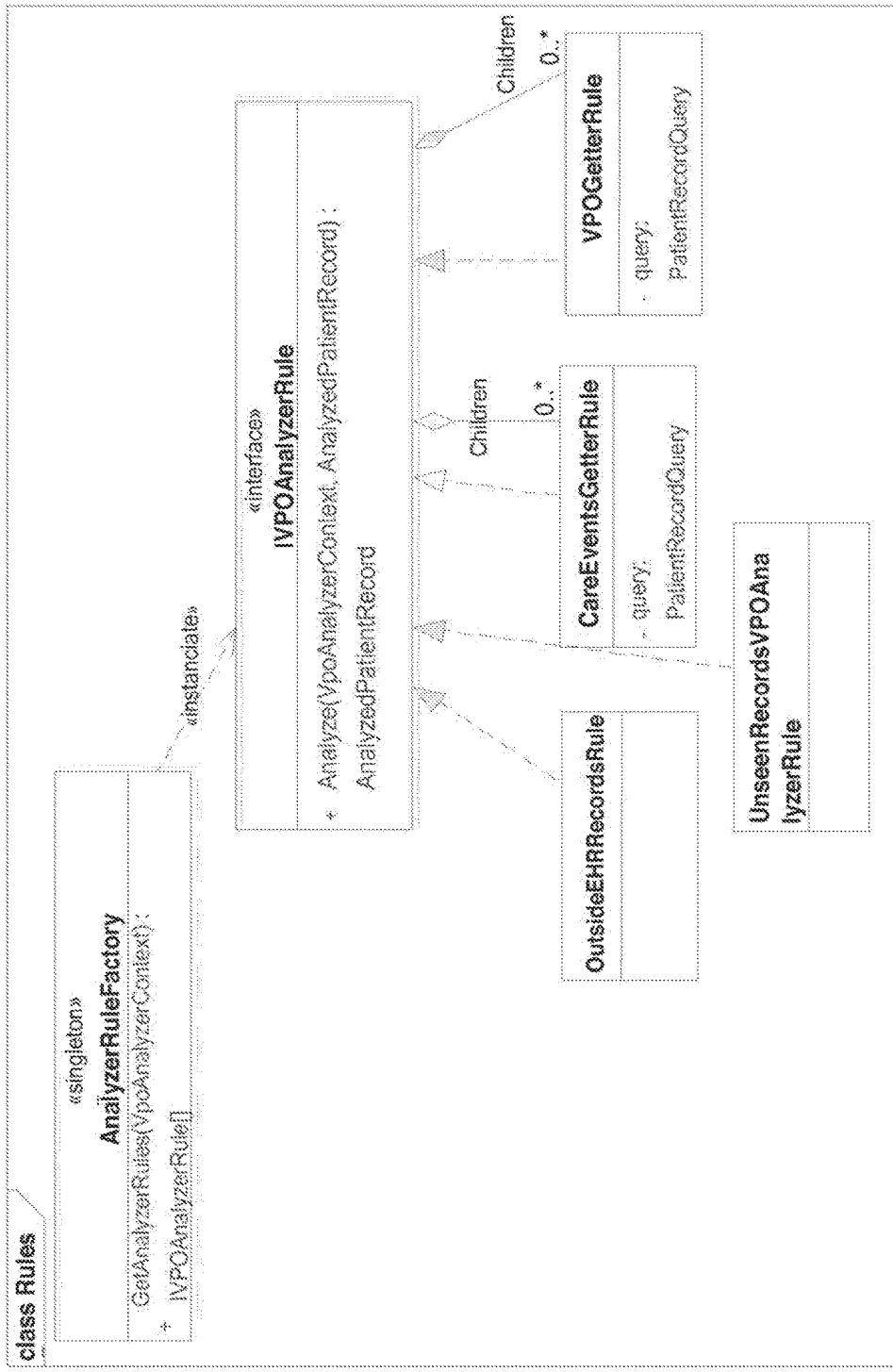
FIG. 27 is an example logical diagram of the rules functionality of FIG. 26.

FIG. 27 is an example logical diagram of the rules functionality of FIG. 26. The AnalyzerRuleFactory functionality of FIG. 27 typically comprises a singelton class, serving as a factory for analyzer rules, based on configuration. The configuration may be based on CareManagement suite, which in turn may allow configuring different profiles and personalization. The CareEventsGetterRule functionality of FIG. 27 typically comprises an analyzer "rule" which gets CareEvents based on a CareEvents query (which events are of interest? how far back?). It may merge its results to the upper level. The OutsideEHRRecordsRule functionality of FIG. 27 typically comprises an analyzer which highlights those records which are out of reach in a given EMR. The rule may be based on system links configuration, which may be part of the PPOL of FIG. 15. The UnseenRecordsVPOAnalyzerRule functionality of FIG. 27 typically highlights those records the user have not seen yet, based on information about entry to health information exchange system (HIES) applications, for example PLV records. The VPOGetterRule functionality of FIG. 27 typically comprises an analyzer "rule" which is based on VPO query and a set of child analyzer rules which further analyze the fetched VPO. The VPOGetterRule functionality of FIG. 27 typically merges its results to the upper level.

Figure 28:
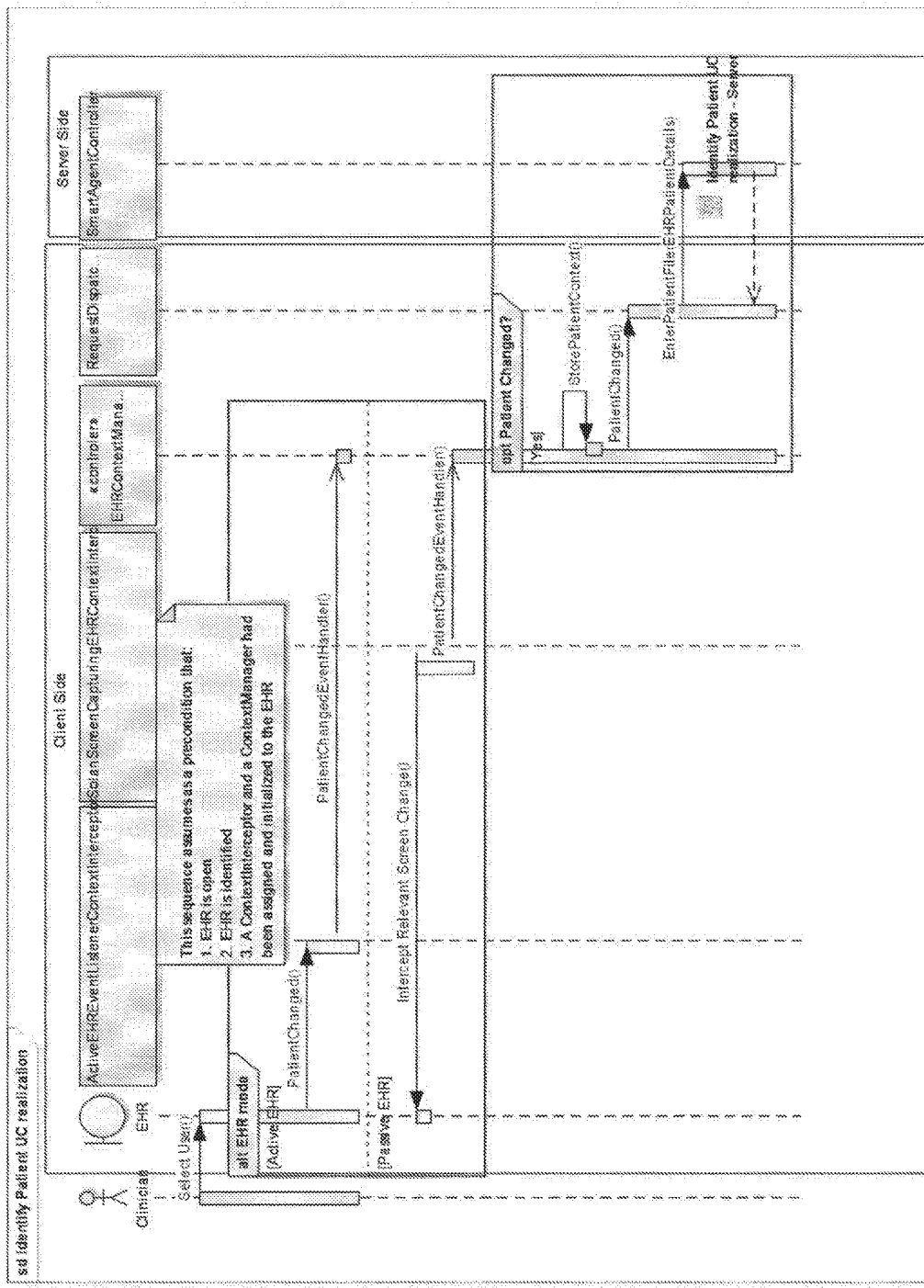
FIG. 28 is an Identify Patient UC (use case) realization sequence diagram illustrating an example Use Case (UC) Realization process.
Figure 29:
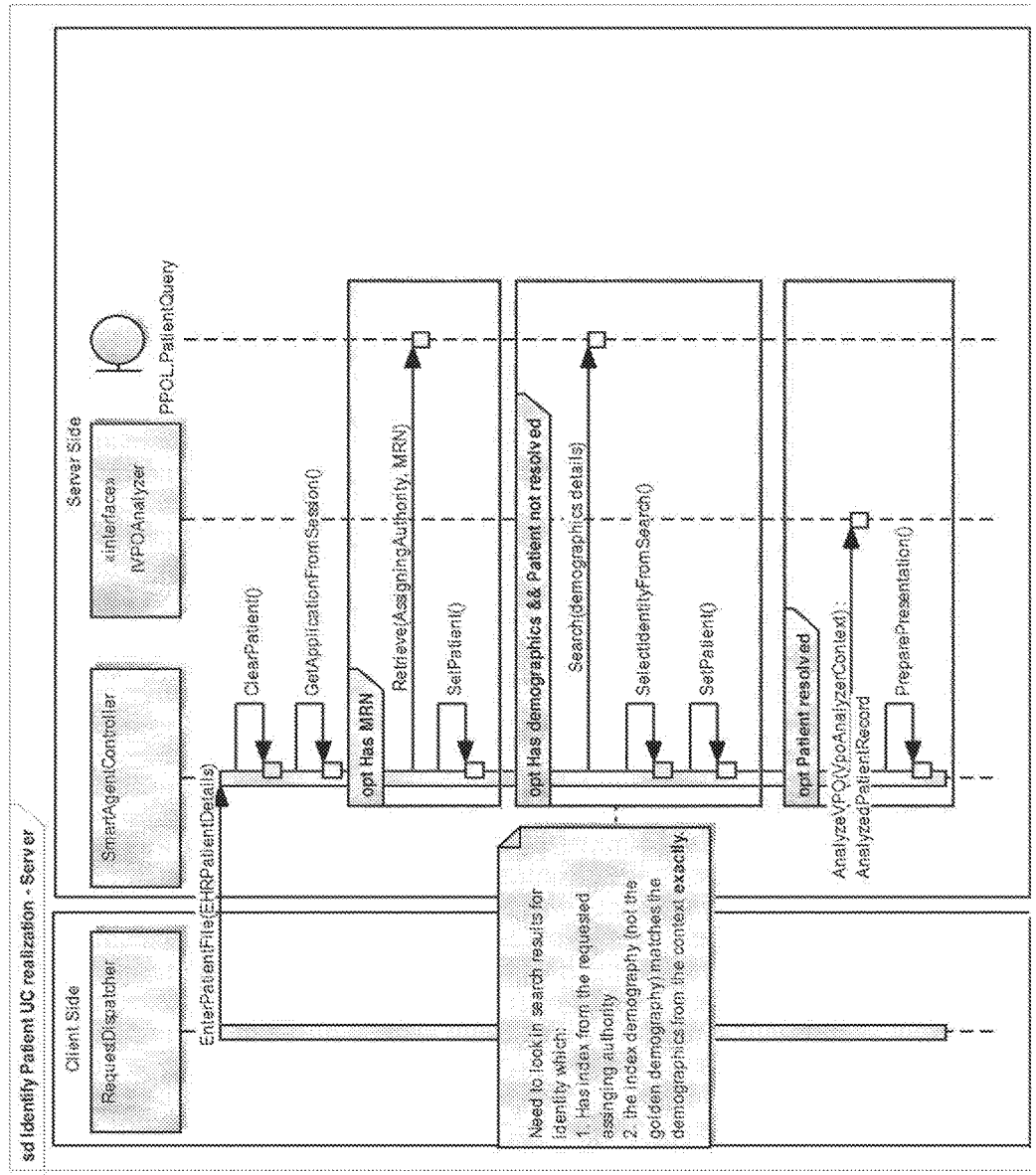
FIG. 29 is a sequence diagram of an example server operative to identify patient UC realization.

An example Use Case (UC) Realization process is illustrated in the Identify Patient UC realization sequence diagram of FIG. 28. An example server operative to Identify Patient UC realization is illustrated in the sequence diagram of FIG. 29.

A particular advantage of certain embodiments of the present invention is that the EMR's code need not be changed because the apparatus of the present invention is able to intercept whatever context it employs from the EMR. Any suitable method may be employed for intercepting EMR context, such as but not limited to:

a. use of a context management protocol such as CCOW.

b. screen capturing (also termed herein "screen scrapping")

c. providing a specialized context interception adaptor, also termed herein "interceptor" for a particular EMR taking advantage of a specific context sharing capability which that particular EMR has. Typically, the architecture of the system shown and described herein includes one or more adaptors for context interception also termed herein "interceptors", e.g. as shown in FIG. 23, and therefore any such special adaptor can easily be incorporated into the architecture of the system shown and described herein, as an additional or substitute adaptor in FIG. 23.

Figure 32:
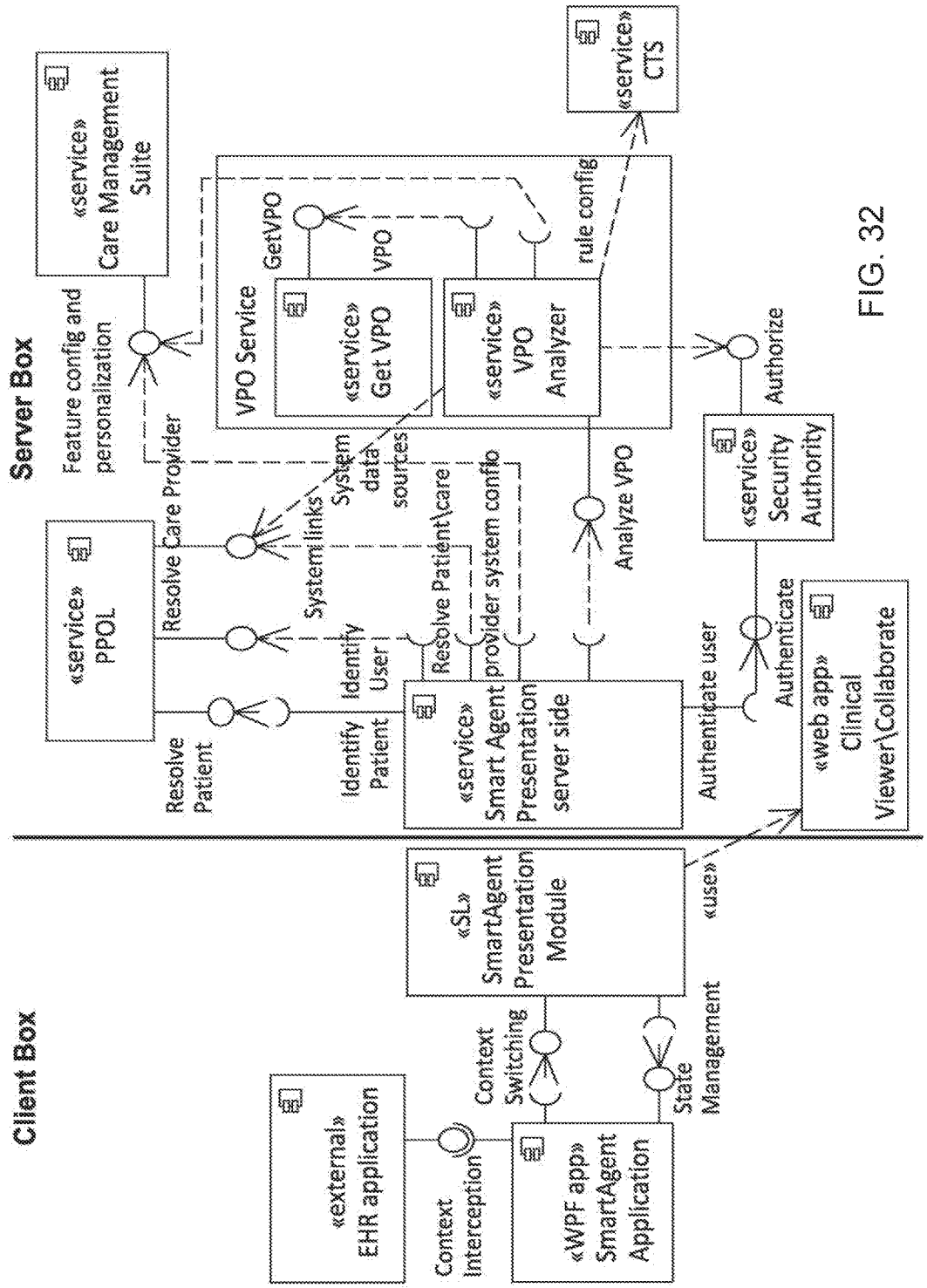
FIG. 32 is a simplified functional block diagram illustration of an embodiment of the invention showing a smart agent which may be constructed and operative in accordance with any of the embodiments shown and described herein.

FIG. 32 is a simplified functional block diagram illustration of an embodiment of the invention showing a smart agent which may be constructed and operative in accordance with any of the embodiments shown and described herein, operative in conjunction with an HIE which may comprise any conventional HIE such as but not limited to DBMotion's HIE; and one or more conventional EMRs (EHRs).

The smart agent of FIG. 32 may include a client and server as shown; however, functionalities of these two may be interchanged as desired. Any suitable functional connection between the SmartAgent and the Entity Identity Management (EMPI) may be provided such as that described above with reference to FIGS. 11 and/or 15. Any suitable functional connection between the SmartAgent and Security Services may be provided such as that described above with reference to FIGS. 14 and/or 15. Any suitable functional connection between the SmartAgent and Patient Data Services may be provided such as that described above with reference to FIG. 15. Any suitable interceptors may be employed such as the Context Interceptor processor described above with reference to FIG. 13. The Client may be based in part on the apparatus of FIG. 16 including the ScreenScraping functionality which may include a context interceptor, SmartAgent Host and SmartAgent presentation client as described herein. The SmartAgent Client may optionally be based on the Context Interceptor described hereinabove with reference to any or all of FIGS. 17, 21 and 23. A suitable object model of the context which the context interceptor API of FIG. 32 may employ, is described above with reference to FIG. 17. The Web service component of the server may for example comprise the SmartAgent Presentation Server of FIG. 16 as described above. The VPO analyzer component of the server may for example be implemented in accordance with the apparatus of FIG. 24.

FIG. 30 is a top-level simplified flowchart illustration of a method of operation for the smart agent system of FIG. 1*a*, according to an embodiment of the present invention.

Figure 33:
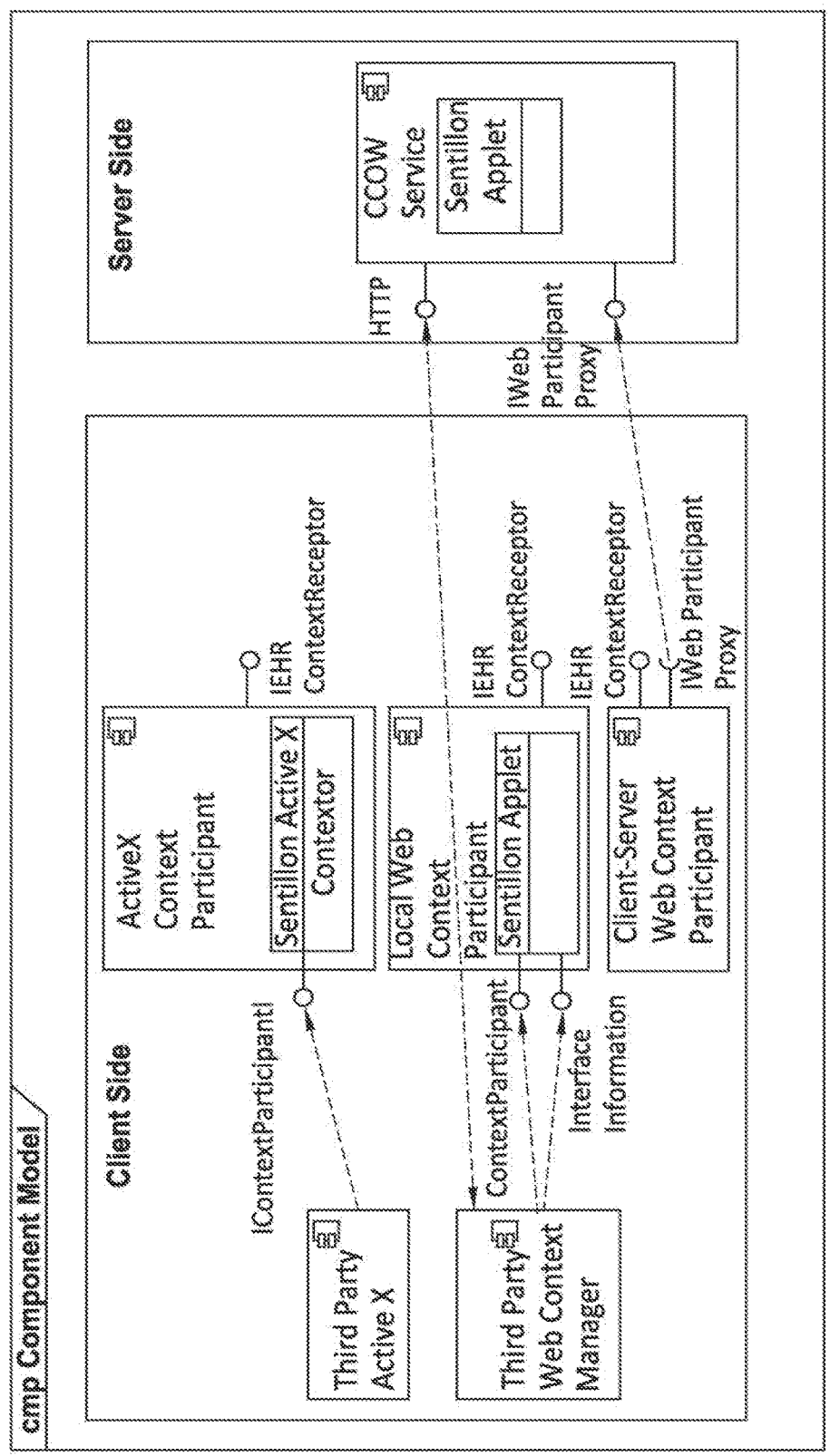
FIG. 33 is a diagram illustration of an example CCOW context Interceptor according to certain embodiments.

FIG. 33 is a diagram illustration of an example CCOW context Interceptor according to certain embodiments.

Figure 34:
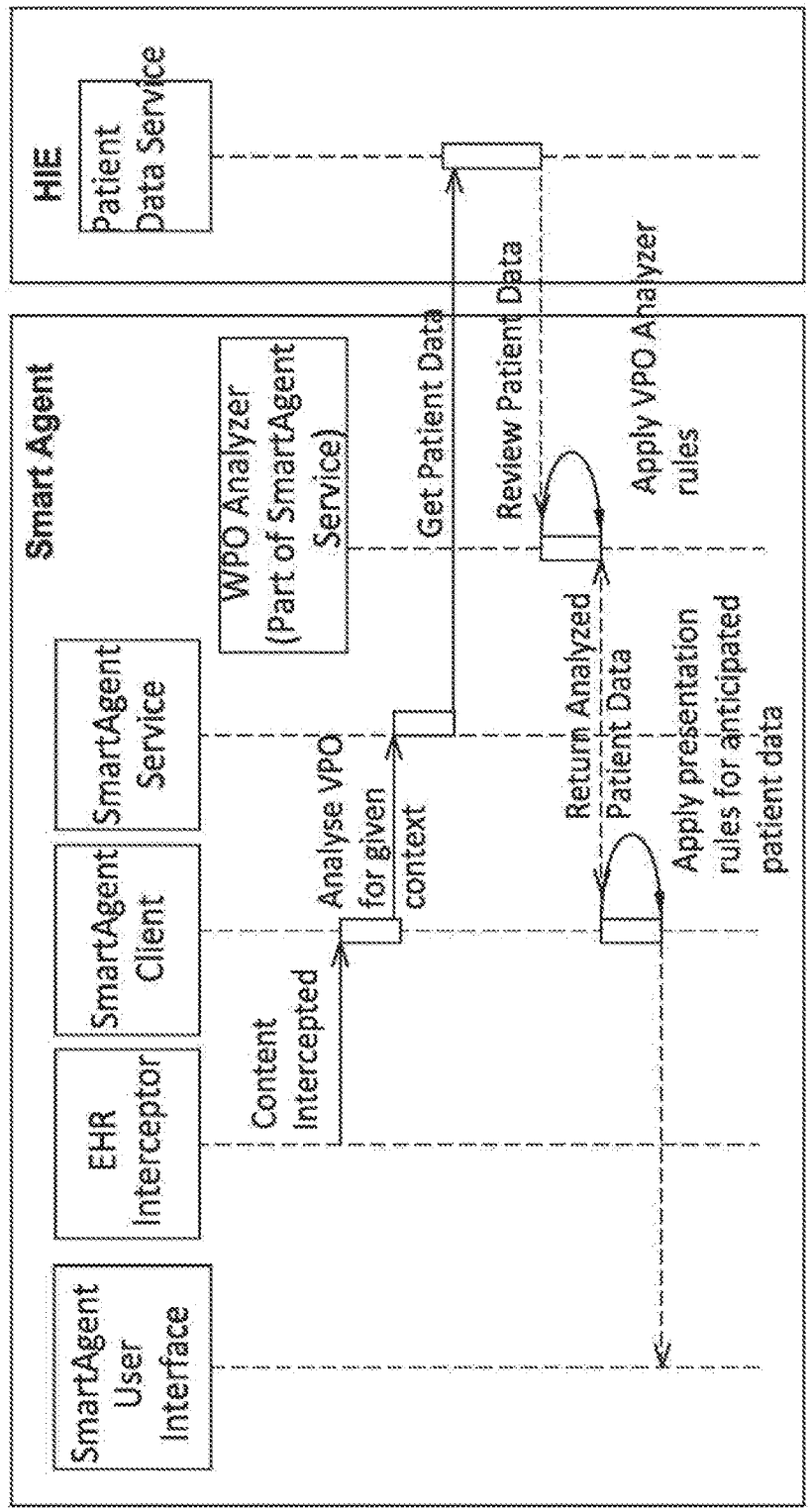
FIG. 34 is a diagram illustrating filtering of clinical information whose source of information is a given EMR according to certain embodiments.

FIG. 34 is a diagram illustrating filtering of clinical information whose source of information is a given EMR according to certain embodiments.

It is appreciated that software components of the present invention including programs and data may, if desired, be implemented in ROM (read only memory) form including CD-ROMs, EPROMs and EEPROMs, or may be stored in any other suitable typically non-transitory computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code, such as executable code, having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; electronic devices each including a processor and a cooperating input device and/or output device and operative to perform in software any steps shown and described herein; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any step described herein may be computer-implemented. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (b) outputting the solution.

Features of the present invention which are described in the context of separate embodiments may also be provided in combination in a single embodiment. Conversely, features of the invention, including method steps, which are described for brevity in the context of a single embodiment or in a certain order may be provided separately or in any suitable subcombination or in a different order. "e.g." is used herein in the sense of a specific example which is not intended to be limiting. Devices, apparatus or systems shown coupled in any of the drawings may in fact be integrated into a single platform in certain embodiments or may be coupled via any appropriate wired or wireless coupling such as but not limited to optical fiber, Ethernet, Wireless LAN, HomePNA, power line communication, cell phone, PDA, Blackberry GPRS, Satellite including GPS, or other mobile delivery. It is appreciated that in the description and drawings shown and described herein, functionalities described or illustrated as systems and sub-units thereof can also be provided as methods and steps therewithin, and functionalities described or illustrated as methods and steps therewithin can also be provided as systems and sub-units thereof. The scale used to illustrate various elements in the drawings is merely exemplary and/or appropriate for clarity of presentation and is not intended to be limiting.

What is claimed is:

1. A method executed by a processor of a computerized device for providing first health information of a patient from an electronic medical records (EMR) application of an EMR system with second health information for the patient from a health information exchange (HIE) system for concurrent view by a health provider, the method comprising:

running, on the computerized device, an agent application instance that is bound to an EMR application instance running on the computerized device;

responsive to the EMR application instance running on the computerized device acquiring first health information of the patient from the EMR system of the EMR application and displaying the first health information within a first graphical user interface (GUI) generated by the EMR application instance running on the computerized device, the first GUI included in a display window, capturing a context for the first health information, wherein the context includes a patient identifier for the patient, a health provider identifier for the health provider, and an identifier for the EMR system;

transmitting the context to a web service executing on a server computing device, wherein the web service retrieves the second health information for the patient from the HIE system based upon the context, and further wherein the web service applies a rule to the second health information to generate filtered second health information, the filtered second health information failing to include data that is also included in the first health information;

responsive to receiving the filtered second health information from the web service, displaying the filtered second health information within a second GUI generated by the agent application instance running on the computerized device, wherein the second GUI generated by the agent application instance is bound and included in the display window comprising the first GUI generated by the EMR application instance such that the filtered second health information of the patient from the HIE system is displayed concurrently with the first health information of the patient from the EMR system; and responsive to detecting a position change of the display window, repositioning the second GUI within the display window such that the second GUI remains bound within the display window.

2. The method of claim 1, further comprising mimicking, by the agent application instance, a display operation of the display window comprising the first GUI generated by the EMR application instance such that when the display window comprising the first GUI generated by the EMR application instance is minimized, the second GUI generated by the agent application instance also is minimized concurrently therewith.

3. The method of claim 1, further comprising mimicking, by the agent application instance, a display operation of the display window comprising the first GUI generated by the EMR application instance such that when the display window comprising the first GUI generated by the EMR application instance is moved, the second GUI generated by the agent application instance also is moved concurrently therewith.

4. The method of claim 1, wherein the second GUI generated by the agent application instance is comprised by a second display window that is displayed on top of the display window comprising the first GUI generated by the EMR application instance.

5. The method of claim 1, further comprising mimicking docking of the second GUI generated by the agent application instance within the display window comprising the first GUI generated by the EMR application instance.

6. The method of claim 1, wherein the second health information of the patient acquired from the HIE system is determined to be duplicative of the first health information of the patient from the EMR system based on defined semantic relationships.

7. The method of claim 1, wherein the second GUI generated by the agent application instance is transitionable between an expanded view for viewing of the filtered second health information of the patient from the HIE system with the first health information of the patient from the EMR system, and a collapsed view for viewing of the first health information of the patient from the EMR system without viewing the filtered second health information of the patient from the HIE system.

8. The method of claim 7, further comprising providing a flashing alert by the agent application instance when the second GUI is not in the expanded view indicating that the health provider should transition the second GUI to the expanded view.

9. The method of claim 8, wherein the flashing alert is provided by the agent application instance when the filtered second health information of the patient that is not from the EMR system has been acquired from the HIE system.

10. The method of claim 1, wherein the agent application instance selectively displays the filtered second health information of the patient acquired from the HIE system.

11. The method of claim 10, wherein the agent application instance filters from display health information of the patient acquired from the HIE system that is from the EMR system.

12. The method of claim 11, further comprising selectively enabling and disabling through a user control filtering of the health information of the patient by the agent application instance.

13. The method of claim 1, further comprising determining the context by screen scraping by the agent application instance information displayed by the EMR application instance.

14. The method of claim 1, further comprising determining by the agent application instance a use context within the EMR application instance.

15. The method of claim 1, further comprising determining by the agent application instance a current workflow context within the EMR application instance.

16. The method of claim 1, further comprising providing, by the agent application instance, event notifications for view by the health provider.

17. The method of claim 1, further comprising acquiring and displaying by, the agent application instance, third health information from the HIE system for a population of patients.

18. A computerized device comprising:
a processor;
memory storing instructions, wherein the instructions, when executed by the processor, are configured to cause the processor to perform acts comprising:
running, on the computerized device, an agent application instance that is bound to an electronic medical records (EMR) application instance running on the computerized device;
responsive to the EMR application instance running on the computerized device, acquiring first health information of a patient from an EMR system of the EMR application instance and displaying the first health information within a first graphical user interface (GUI) generated by the EMR application instance running on the computerized device, the first GUI included in a display window;

capturing a context for the first health information, wherein the context includes a patient identifier for the patient, a health provider identifier for a health provider, and an identifier for the EMR system;

transmitting the context to a web service executing on a server computing device, wherein the web service retrieves second health information for the patient from a health information exchange (HIE) system based upon the context, and further wherein the web service applies a rule to the second health information to generate filtered second health information, the filtered second health information failing to include data that is also included in the first health information;

responsive to receiving the filtered second health information from the web service, displaying the filtered second health information within a second GUI generated by the agent application instance running on the computerized device, wherein the second GUI generated by the agent application instance is bound and included in the display window comprising the first GUI generated by the EMR application instance such that the filtered second health information of the patient from the HIE system is displayed concurrently with the first health information of the patient from the EMR system; and responsive to detecting a position change of the display window, repositioning the second GUI within the display window such that the second GUI remains bound within the display window.

19. A computer-readable storage medium comprising instructions that, when executed by a processor of a computerized device, causes the processor to perform acts comprising:

running, on the computerized device, an agent application instance that is bound to an electronic medical records (EMR) application instance running on the computerized device;

responsive to the EMR application instance running on the computerized device acquiring first health information of a patient from an EMR system of the EMR application instance and displaying the first health information within a first graphical user interface (GUI) generated by the EMR application instance running on the computerized device, the first GUI included in a display window;

capturing a context for the first health information, wherein the context includes a patient identifier for the patient, a health provider identifier for a health provider, and an identifier for the EMR system;

transmitting the context to a web service executing on a server computing device, wherein the web service retrieves second health information for the patient from a health information exchange (HIE) system based upon the context, and further wherein the web service applies a rule to the second health information to generate filtered second health information, the filtered second health information failing to include data that is also included in the first health information;

responsive to receiving the filtered second health information from the web service, displaying the filtered second health information within a second GUI generated by the agent application instance running on the computerized device, wherein the second GUI generated by the agent application instance is bound and included in the display window comprising the first GUI generated by the EMR application instance such that the filtered second health information of the patient from the HIE system is displayed concurrently with the first health information of the patient from the EMR system; and responsive to detecting a position change of the display window, repositioning the second GUI within the display window such that the second GUI remains bound within the display window.

20. The method of claim 1, wherein repositioning the second GUI within the display window such that the second GUI remains bound within the display window comprises:

loading anchor parameters for the EMR application instance from a configuration file, the anchor parameters comprising:
  a first anchor point indicating a first corner of the display window to use as a first reference point;
  a second anchor point indicating a second corner of the second GUI to use as a second reference point;
  a horizontal offset indicating a first number of pixels that the second anchor point is to be horizontally offset from the first anchor point;
  a vertical offset indicating a second number of pixels that the second anchor point is to be vertically offset from the first anchor point; and
repositioning the second GUI based upon the anchor parameters.

* * * * *